(12) United States Patent
Csizmadia et al.

(10) Patent No.: US 9,650,664 B2
(45) Date of Patent: May 16, 2017

(54) USE OF PHOTOCLEAVABLE COMPOUNDS

(71) Applicant: FEMTONICS KFT, Budapest (HU)

(72) Inventors: Imre Gyula Csizmadia, Szeged (HU); Zoltan Mucsi, Budapest (HU); Gergely Szalay, Budapest (HU); Attila Kaszas, Budapest (HU); Csilla Lukacsne Haveland, Budapest (HU); Orsolya Majercsik, Budapest (HU); Attila Potor, Nadudvar (HU); Gergely Katona, Budapest (HU); Jozsef Balazs Rozsa, Budapest (HU); Dorina Gundisch, Budapest (HU); Balazs Chiovini, Kecskemet (HU); Denes Palfi, Szeged (HU)

(73) Assignee: Femtonics KFT, Budapest (HU)

( * ) Notice: Subject to any disclaimer, the term of this patent is extended or adjusted under 35 U.S.C. 154(b) by 163 days.

(21) Appl. No.: 14/348,903

(22) PCT Filed: Oct. 3, 2012

(86) PCT No.: PCT/HU2012/000100
§ 371 (c)(1),
(2) Date: Apr. 1, 2014

(87) PCT Pub. No.: WO2013/050798
PCT Pub. Date: Apr. 11, 2013

(65) Prior Publication Data
US 2014/0234883 A1    Aug. 21, 2014

(30) Foreign Application Priority Data

Oct. 3, 2011 (HU) .................... 1100550
Dec. 20, 2011 (WO) ............ PCT/HU2011/000129

(51) Int. Cl.
| | | |
|---|---|---|
| *C12Q 1/52* | (2006.01) | |
| *C07D 209/08* | (2006.01) | |
| *C07D 209/14* | (2006.01) | |
| *C07D 209/20* | (2006.01) | |
| *C12Q 1/32* | (2006.01) | |

(52) U.S. Cl.
CPC ............ *C12Q 1/52* (2013.01); *C07D 209/08* (2013.01); *C07D 209/14* (2013.01); *C07D 209/20* (2013.01); *C12Q 1/32* (2013.01)

(58) Field of Classification Search
None
See application file for complete search history.

(56) References Cited

U.S. PATENT DOCUMENTS

| | | |
|---|---|---|
| 6,765,014 B1 | 7/2004 | Corrie et al. |
| 7,737,169 B2 | 6/2010 | Corrie et al. |
| 7,812,017 B2 * | 10/2010 | Angbrant ............. C07D 209/08 514/231.2 |
| 8,642,785 B2 | 2/2014 | Ellis-Davies |
| 2004/0171846 A1 | 9/2004 | Corrie et al. |
| 2007/0167353 A1 * | 7/2007 | Hilfinger ............ A61K 31/7076 514/1.2 |
| 2007/0203099 A1 | 8/2007 | Corrie et al. |
| 2010/0096252 A1 | 4/2010 | Ellis-Davies |
| 2012/0016103 A1 * | 1/2012 | Borelli ..................... C07K 7/02 530/329 |
| 2012/0283191 A1 * | 11/2012 | Hansson ............. A61K 38/1709 514/15.7 |

FOREIGN PATENT DOCUMENTS

| | | |
|---|---|---|
| WO | 00/55133 A1 | 9/2000 |
| WO | 02/083639 A1 | 10/2002 |
| WO | 2008/094922 A1 | 8/2008 |

OTHER PUBLICATIONS

Canepari et al. J. Neuroscience Methods (2001) 112: 29-42.*
International Search Report from PCT/HU2012/000100 dated Aug. 12, 2013.
Chicheng Ma et al. "Photochemical Cleavage and Release of Carboxylic Acids from alpha-Keto Amides" Journal of Organic Chemistry, [2005], vol. 70, No. 11, pp. 4431-4442.
Alfred Hassner et al. "Light-Sensitive Protecting Groups for Amines and Alcohols: The Photosolvolysis of N-Substituted 7-Nitroindolines" Synlett, [2007], No. 15, pp. 2405-2409.
George Papageorgiou et al. "Synthetic and photochemical studies of substituted 1-acyl-7-nitroindolines" Photochemical & Photobiological Sciences, [2005], vol. 4, No. 11, pp. 887-896.
Jean-Luc Debieux et al. "Preparation of Photoactivable Amino Acid Derivatives" Journal of Organic Chemistry, [2009], vol. 74, No. 12, pp. 4519-4524.

(Continued)

*Primary Examiner* — Susan Hanley
(74) *Attorney, Agent, or Firm* — Millen White Zelano & Branigan, P.C.

(57) ABSTRACT

Use of photochemically cleavable compounds in course of one or multi-photon irradiation experiments.

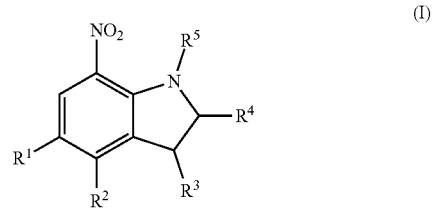

(I)

13 Claims, 5 Drawing Sheets

(56) References Cited

OTHER PUBLICATIONS

Zhou Zhang et al. "Pre-steady-State Currents in Neutral Amino Acid Transporters Induced by Photolysis of a New Caged Alanine Derivative" Biochemistry, [2007], vol. 46, No. 12, pp. 3872-3880.
George Papageorgiou et al. "Synthesis and photolytic evaluation of a nitroindoline-caged glycine with a side chain of high negative charge for use in neuroscience" Elseveier, Tetrahedron, [2011], vol. 67, No. 29, pp. 5228-5234.
George Papageorgiou et al. "Synthesis and photolytic evaluation of a nitroindoline-caged glycine with a side chain of high negative charge for use in neuroscience" Tetrahedron, [2011], vol. 67, No. 29, pp. 1-11.
Gilberto Goissis et al. "Synthesis of protected peptide acide and esters by photosolvolysis of 1-peptidy1-5-bromo-7-nitroindolines" Chemical Abstracts Service, Caplus, [1977], pp. 1-7.
Hungarian Search Report related to corresponding Hungarian Patent Application No. P1100550 dated Feb. 22, 2012.
James Morrison et al. "Mechanisms of photorelease of carboxylic acids from 1-acyl-7-nitroindolines in solutions of varying water content" Photochem. PHotobiol. Sci., [2002], vol. 1, pp. 960-969.
George Papageorgiou et al. "Regioselective nitration of 1-acyl-4-methoxyindolines leads to efficient synthesis of a photolabile L-glutamate precursor" Synthetic Communications, [2002], vol. 32, No. 10, pp. 1571-1577.
Olesya D. Fedoryak et al. "Synthesis of a caged glutamate for efficient one-and two-photon photorelease on living cells" Chemical Communications, [2005], vol. 29, pp. 3664-3666.
George Papageorgiou et al. "Photorelease of Carboxylic Acids from 1-Acyl-7-nitroindolines in Aqueous Solution: Rapid and efficient photorelease of L-glutamate" Journal of American Chemical Soc., [1999], vol. 121, pp. 6503-6504.
M. Canepari et al. "Photochemical and pharmacological evaluation of 7-nitroindolinyl-and 4-methoxy-7-nitroindolinyl-amino acids as novel, fast caged neurotransmitters" Journal of Neuroscience Methods, [2001], vol. 112, pp. 29-42.

\* cited by examiner

FIG. 5A  FIG. 5B

USE OF PHOTOCLEAVABLE COMPOUNDS

SUBJECT OF THE INVENTION

The present invention relates to the use of photocleavable compounds, the so called "caged compounds" or salts thereof in one or multiphoton irradiation experiments together with such reagents which are capable to neutralize the bioactive compounds formed by the spontaneous degradation of photocleavable compounds.

TECHNICAL BACKGROUND OF THE INVENTION

The photocleavable compounds, the so called "caged reagents" are very useful compounds in the course of investigation of biological processes. Such reagents and the use thereof are described particularly in the description of EP 1 757585 A1 and U.S. Pat. No. 6,765,014 by the inventors and in the articles of Morrison et al. (Photochemical & Photobiological Sciences, (2002), 1, 960), M. Canepari et al. (J. Neurosci Methods, (2001), 112, 29), M. Canepari et al. (J. Physiol., (2001), 533, 765). These compounds are biologically inactive but due to light these compounds cleave and biologically active compounds evolve. These compound evolve fast due to UV or visible light. These photocleavable compounds can be used for delivering the biologically active compounds, such us neuroactive amino acids to the place where their activity is necessary. The release of active compounds from photocleavable compounds using one- or multi-photon irradiation method, preferably two-photon irradiation method is a dynamically developing method of researches of neurons as it is described by Fedoryak et al. in their article (*Chemical Communications*, (2005), 29, 3664-3666). In the course of a multi-photon irradiation process the photochemical reaction is carried out by excitation of two or more photons. With the use of these methods the stimulation of neurons can be carried out locally and very specifically. The above-mentioned documents disclose the release of glutamic acid and gamma-amino-butiric acid (GABA) from photocleavable derivatives thereof using mono- or two-photon irradiation processes. The photocleavable compounds were used as bases in all cases. In the published patent application No. EP 1757585 and in the U.S. Pat. No. 6,765,014 7-indoline compounds are described which are used as photocleavable reagents. In these documents the photocleavable compounds are described as bases or salts formed with cations. In the publication of the patent application No. WO2008/094922 di-nitro derivatives are described as base or salts with cations.

The [2-amino-5-(4-methoxy-7-nitro-2,3-dihydro-indol-1-yl)-5-oxo-pentanoic acid (hereinafter as "MNI-Glu") is a mononitroindoline (MNI) derivative which contains a glutamic acid component and is a well known and useful compound for the multi-photon irradiation examinations of the nervous system. However, the quantum yield of these mono-nitro-indoline derivatives is low and the release of active amino acids is also relatively slow and the maximum of their photon absorption is also not ideal. A higher quantum yield can be achieved with the use of dinitro-indol derivatives, such as the compounds based on the structure of the 4-methoxy-5,7-dinitro-2,3-dihydro-1H-indol. Such compounds are e.g. the 2-amino-5-(4'-methoxy-5',7'-dinitro-2',3'-dihydro-indol-1-yl)-5-oxo-pentanoic acid (hereinafter as "DNI-Glu") which is disclosed by Fedoryak et al. (*Chemical Communications*, (2005), 29, 3664-3666), G. C. R. Ellis-Davies et al. (*The Journal of Neuroscience*, Jun. 20, (2007), 27(25), 6601-6604) and G. Papageorgiou et al. (*Photochemical & Photobiological Sciences*, (2005), 4(11), 887-896). The biological experiments are not disclosed in these articles but only the preparation of the analogue compounds is disclosed. The preparation of DNI-Glu according to Fedoryak et al. is carried out by a two-step nitration. At first the 2-amino-5-(4-methoxy-2,3-dihydro-indol-1-yl)-5-oxo-pentanoic acid which was protected on its amino and carboxyl groups was prepared then nitrated at the position 7. The mono-nitro derivative was nitrated at the position 5 in the next step. Subsequently, the protecting groups were removed, thus the product named DNI-Glu was obtained. A similar process is described in the patent application No. WO2008/094922. According to the inventors the effective process for the preparation of DNI-Glu requires an appropriate purity of the unprotected mono-nitro amino acid for the second nitration step. Thus the second nitro group can be introduced only in a second step. It was found that the dissolution of DNI-Glu is so bad in physiological solutions that in two-photon irradiation experiments of hippocampus neurons no electrical signals had been arisen. A further problem was that the DNI-Glu separated from the frozen buffer and could not be dissolved when it was warmed up to room temperature. These problems were eliminated by the insertion of a carboxy-methoxy group at the position 4 of the DNI-Glu according to the patent application. The 4-carboxy-methoxy-5,7-dinitrindolinyl-Glu (hereinafter CDNI-Glu) was prepared by a two-step nitration process. The CDNI-Glu compound was prepared only with a yield of 6.9% based on the indol derivative. Thus, according to the prior art the much better quantum yields of DNI derivatives could not be utilized because such stable derivatives could not be prepared which were appropriate stable either during storage or during the biological tests. Thus these reagents could not be prepared on industrial scale because their industrial manufacture and the preservation of their stability were not solved. Furthermore, there was no solution for the elimination of the interferences in the tests caused by biologically active compounds which spontaneously formed from easily degradable DNI derivatives. The known photochemically cleavable compounds, the so-called "caged" compounds applicable in examination processes were used only in the form of a base, but some of them were prepared also as a metal salt. These compounds have several disadvantageous properties. In the form of a base it is difficult to handle them, they are usually hygroscopic, light sensitive and labile. The photocleavable compounds hydrolyse spontaneously in the conditions of the experiments in many cases and the releasing active compounds interfere the experiment. It is a known fact that the neuroactive amino acids and amines are released quickly during the biological processes. Therefore the so-called "caged" compounds can be a good model of the physiological processes which degrade rapidly by the effect of irradiation. But these compounds more and more tend to hydrolyse during the experiment as well, therefore a considerable amount of amino acid or neuroactive amine gets into the measuring media, in the intercellular fluidum among the neurons before the irradiation. This is especially true for the DNI compounds which have a high quantum yield. Above a certain threshold these compounds can sensibilize the neurons, give a false result of the experiment, and in a higher concentration they may even cause the death of the examined neurons.

It has been a need for the preparation of such photocleavable compounds or the change of the used experimental conditions enabling the elimination of the above-mentioned disadvantages, so the cleavage of the "caged" compounds be fast, but the compounds resulted of the spontaneous hydrolysis do not disturb the measurement.

ESSENCE OF THE INVENTION

The present invention relates to the use of photocleavable compounds or salts thereof together with reagents for neutralisation of the biologically active compounds which release from the photocleavable compounds in mono- or multi-photon irradiation experiments.

We found that in the case of using a reagent which neutralises the biologically active compound in the course of the mono- or multi-photon irradiation experiments the reproducibility of the tests is considerably better and it makes possible to study a broad selection of biological active compounds.

DETAILED DESCRIPTION OF THE INVENTION

According to the present invention the photochemically cleavable compounds or salts thereof and the reagents for neutralizing the biologically active compounds which evolve from the photocleavable compounds are used together in one- and multiphoton irradiation tests.

According to an advantageous embodiment of the present invention the photochemically cleavable compound releases amino acids, neuroactive amines, neurotransmitters, hormones, DNA, RNA, or DNA or RNA fragments, peptides, lipids, secondary signal compounds, pharmaceutically active ingredients or candidates thereof as a biological active compound.

Neurotransmitters are for example glycin, asparagin acid (L-Asp), Glutamic acid (L-Glu), Gamma-aminobutyric acid (GABA), Hystamine, Dopamine, Adrenaline, Noradrenaline, Serotonin, etc.

Candidates of pharmaceutically active agents are such compounds which are assumed to be a biologically active compound and the activity of the compound can be tested with the process according to the present invention. Such compounds are e.g. the compounds which act on the central nervous system.

An advantageous embodiment of the present invention is the use of compounds of the general formula (I)

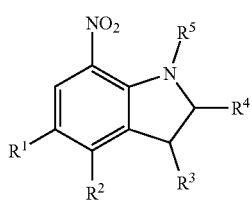

(I)

wherein
$R^1$ stands for a hydrogen atom, or an electron withdrawal group, preferably cyano, nitro, carboxyl or formyl group or a halogen atom;
$R^2$ stands for a hydrogen atom, hydroxy group, halogen atom, preferably bromo atom or an unsubstituted straight or branched, saturated or unsaturated alkoxy, cycloalkoxy, preferably $C_1$-$C_6$ alkoxy group or
a straight or branched substituted alkoxy, cycloalkoxy, preferably $C_1$-$C_6$ alkoxy group, which has one or two identical or different unsubstituted $C_1$-$C_6$ alkyl group(s), aryl group, heteroaryl group or cycloalkyl group; or an unsubstituted amino group or a substituted amino group, preferably dimethylamino-$C_1$-$C_6$ alkoxy group, or a straight or branched carbon chained substituted saturated or unsaturated alkoxy, cycloalkoxy, preferably $C_1$-$C_6$ alkoxy group substituted with one ore more carboxyl group, preferably a malonyl-oxy group; or an unsubstituted amino group, or an amino group substituted with one $C_1$-$C_6$ alkyl group or cycloalkyl group, or two identical or different $C_1$-$C_6$ alkyl groups, aryl group, heteroaryl group or cycloalkyl group;
$R^3$ stands for a hydrogen atom, or a substituted or unsubstituted alkyl group, or
$R^2$ and $R^3$ together stand for an unsubstituted cycloalkyl group;
$R^4$ stands for a hydrogen atom or a substituted or unsubstituted alkyl group, or $R^3$ and $R^4$ together stand for an unsubstituted cycloalkyl group;
$R^5$ stands for a biologically active compound covalently attached to the nitrogen atom of the indoline ring, or salts thereof formed with organic or inorganic acids in a mono- or multiphoton irradiation experiment together with a reagent which neutralizes the biologically active compound evolved due to spontaneous degradation of the compound of the general formula (I).

The acid addition salts of the compounds can also be used. Salts composed with inorganic acids e.g. hydrochloric acid, nitric acid, sulphuric acid, hydrogen bromide, phosphoric acid, organic acids e.g. saturated or insaturated, substituted or unsubstituted aliphatic carboxylic acids such as formic acid, acetic acid, propionic acid, butyric acid, isobutiric acid, and stearic acid, dacanoic acid, sebacinic acid, orotic acid, palmitic acid, pamoic acid, substituted carboxylic acids such as halogenated carboxylic acids, chloro-acetic acid, dichloroacetic acid, trifluoroacetic acid or oxo-carboxylic acids such as 2-oxo-glutaric acid, pyruvic acid, aliphatic di- and polycarboxylic acids e.g. oxalic acid, adipic acid, succinic acid, fumaric acid, maleic acid, malonic acid, aromatic carboxylic acids, e.g. benzoic acid, salicylic acid, acetylsalicylic acid, 4-aminosalicylic acid, aliphatic or aromatic sulphonic acids such as methane-, ethanesulphonic acid, hydroxy-ethanesulphonic acid, cyclohexyl-sulphonic acid (cyclamic acid), dodecylsulphonic acid, ethane-1,2-disulphonic acid, para-toluenesulphonic acid, naphtalenesulphonic acid, naphthalene-2-sulphonic acid, naphthalene-1,5-disulphonic acid, carbohydrates having carboxyl functions such as glucoheptonic acid, D-gluconic acid, D-glucuronic acid, hydroxyacides such as ascorbinic acid, (+)-L-lactic acid, (±)-DL-lactic acid, malic acid, amino acids, such as L-asparagine acid, preferably unsubstituted $C_1$-$C_4$ carboxylic acids e.g. acetic acid or substituted $C_1$-$C_4$ carboxylic acids having one or more halogen substituents such as dichloroacetic acid, difluoroacetic acid, most preferably trifluoroacetic acid can be used as acid addition salts.

As substituent $R^5$ of the compounds of the general formula (I) according to the present invention, i.e. as a biologically active compound which is covalently linked to the nitrogen atom of the indoline ring DNA, RNA or fragments thereof, hormones, neurotransmitters, amino acids, peptides, lipids or neuroactive amines, pharmaceutically active ingredients or candidates thereof can be used in tests in such a way that reagents capable to neutralise the biologically active compounds formed by the spontaneous hydrolysis of the compounds of the general formula (I) are also used.

According to the present invention the reagents are defined as reagents "capable to neutralise biologically active compounds" which degrade or absorb in a physical, chemical or biological way the biologically active compounds formed by spontaneous hydrolysis of the used "caged" compounds in such a way that these compounds do not accumulate in the reaction mixture. Such compounds can be e.g. enzymes, which convert the amino acids in case of the evolution thereof into a biologically inactive compound, or a cell culture which digests them, or in case of formation of ionic compounds ion change resins can also be used for the absorption of the spontaneously formed biologically active compounds. The selection of the appropriate reagent "capable to neutralise" the biologically active compound depends on the nature of the spontaneously hydrolysed compounds of the "caged" compound.

Co-administration means according to the present invention that during the test beside the "caged" compounds and the further components generally used in the reaction mixture such reagents are also present in the test mixture, preferably in dissolved or suspended or in a solid form, which neutralize the biologically active compounds formed by the spontaneous degradation of the used caged compounds.

According to an advantageous embodiment a trifluoroacetic acid salt of the compound of the general formula (I) is used in a one or a multi-photon, preferably in a two-photon irradiation experiment, co-administered with such reagents, preferably with amino acid degrading enzymes or reagents capable to absorb amino acids in a physical, chemical or biological way, preferably with ion exchange resins, neuron cells, which neutralise the amino acids formed by spontaneous degradation of the compounds of the general formula (I) in which
$R^1$ stands for a nitro group; $R^2$ stands for a hydrogen or bromo atom, or
straight or branched substituted or unsubstituted alkoxy, cycloalkoxy, preferably $C_1$-$C_6$ alkoxy group, substituted with an unsubstituted amino group, or an amino group substituted with a $C_1$-$C_6$ alkyl group or cycloalkyl group, or two identical or different $C_1$-$C_6$ alkyl groups, aryl group, heteroaryl group or cycloalkyl group; or substituted or unsubstituted aryl group;
$R^3$ and $R^4$ stand for hydrogen atom;
$R^5$ is an acid residue of an amino acid or a group of the general formula

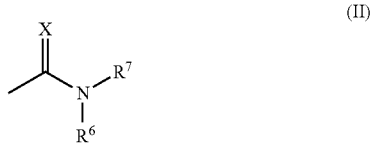

(II)

in which the nitrogen atom and the attached $R^6$ and $R^7$ substituents together stand for an amine residue of a neurotransmitter and X stands for an oxygen or sulphur atom.

According to the most advantageous embodiment a salt composed with trifluoroacetic acid of a compound of the general formula (I) is used in a one or a multi-photon, preferably in a two-photon irradiation experiment, co-administered with such reagents, preferably with amino acid degrading enzymes or reagents capable to absorb amino acids in a physical, chemical or biological way, preferably with ion exchange resins, neuron cells, which neutralise the amino acids formed by spontaneous degradation of the compounds of the general formula (I) in which
$R^1$ stands for a nitro group;
$R^2$ stands for a hydrogen or bromo atom, or dimethylamino-ethoxy group, dimethylamino-propoxy, isomers of dimethylamino-isopropoxy group (—O—CH(CH$_3$)CH$_2$—N(CH$_3$)$_2$ és O—CH$_2$—CH(CH$_3$)—NCH$_3$)$_2$ groups), dimethylamino-isobutoxy group (O—CH$_2$—CH(CH$_3$)—CH$_2$— N(CH$_3$)$_2$; or substituted or unsubstituted aryl group; $R^3$ and $R^4$ stand for a hydrogen atom;
$R^5$ stands for an acid residue of L-Glutamic acid, GABA or Glycin, or a group of the general formula (II) in which the nitrogen atom and the attached $R^6$ and $R^7$ substituents together stand for an amine residue of L-Glutamic acid, GABA or Glycin and X stands for an oxygen or sulphur atom.

Furthermore the present invention relates also to improved one- or multi-photon irradiation processes in which the photocleavable compounds are used together (co-administered) with a reagent which neutralizes the biologically active compounds evolved by spontaneous degradation.

The present invention also refers to compositions which comprises compounds of the general formula (I) and a reagent which neutralises the biologically active compounds formed due to the degradation of the compound of the formula (I) and other accessory agents if necessary.

Further embodiments of the present invention are the trifluoroacetic acid salts of the compounds of the general formula (I) and the process for the preparation thereof, which can be used in one- or multi-photon irradiation experiments and in which
$R^1$ stands for a nitro group;
$R^2$ stands for a hydrogen or bromo atom, or
straight or branched substituted or unsubstituted alkoxy, cycloalkoxy, preferably $C_1$-$C_6$ alkoxy group, substituted with an unsubstituted amino group, or an amino group substituted with a $C_1$-$C_6$ alkyl group or cycloalkyl group, or two identical or different $C_1$-$C_6$ alkyl groups, aryl group, heteroaryl group or cycloalkyl group; or substituted or unsubstituted aryl group;
$R^3$ and $R^4$ stand for a hydrogen atom;
$R^5$ is an acid residue of an amino acid, or a group of the general formula (II)
in which the nitrogen atom and the attached $R^6$ and $R^7$ substituents together stand for an amine residue of an amino acid and X stands for an oxygen or sulphur atom.

Furthermore, the most advantageous embodiment of the present invention relates to the trifluoroacetic acid salts of the compounds of the general formula (I) and the process for the preparation thereof in which $R^1$ stands for a nitro group; $R^2$ stands for a hydrogen or bromo atom, or dimethylamino-ethoxy group, dimethylamino-propoxy, isomers of dimethylamino-isopropoxy group (—O—CH(CH$_3$)CH$_2$—N(CH$_3$)$_2$ és O—CH$_2$—CH(CH$_3$)—N(CH$_3$)$_2$ groups), dimethylamino-isobutoxy group (O—CH$_2$—CH(CH$_3$)—CH$_2$— N(CH$_3$)$_2$; or substituted or unsubstituted aryl group; $R^3$ and $R^4$ stand for a hydrogen atom; $R^5$ stands for an acid residue of L-Glutamic acid, GABA or Glycin, or a group of the general formula (II) in which the nitrogen atom and the attached $R^6$ and $R^7$ substituents together stand for an amine residue of L-Glutamic acid, GABA or Glycin and X stands for an oxygen or sulphur atom.

According to an advantageous embodiment in the trifluoroacetic acid salt of the compound of the general formula (I) $R^5$ is an acid residue of an amino acid or $R^5$ is a group of the general formula (II) in which the nitrogen atom and the attached $R^6$ and $R^7$ substituents together stand for an amine residue of a neurotransmitter or a compound assumed to be a neurotransmitter and X stands for an oxygen or sulphur atom.

We found surprisingly that the trifluoroacetic acid salts of the compound of the general formula (I) with trifluoroacetic acid in which $R^1$ stands for a nitro group;
$R^2$ stands for a hydrogen or bromo atom, or straight or branched substituted or unsubstituted alkoxy, cycloalkoxy, preferably $C_1$-$C_6$ alkoxy group, substituted with an unsubstituted amino group, or with an amino group substituted with a $C_1$-$C_6$ alkyl group or cycloalkyl group, or two identical or different $C_1$-$C_6$ alkyl groups, aryl group, heteroaryl group or cycloalkyl group; or substituted or unsubstituted aryl group;
$R^3$ and $R^4$ stand for a hydrogen atom;
$R^5$ is an acid residue of an amino acid or a group of the general formula (II)
in which the nitrogen atom and the attached $R^6$ and $R^7$ substituents together stand for an amine residue of a neurotransmitter or a compound assumed to be a neurotransmitter and X stands for an oxygen or sulphur atom can be used with a much higher quantum yield than that of e.g. MNI-Glu or its acid addition salt with trifluoroacetic acid (thereafter TFA), the MNI-Glu*TFA. Although these compounds have a higher quantum yield, they readily degrade spontaneously in the experimental conditions. Surprisingly, the released amino acids or neurotransmitters could be neutralized with the addition of suitable reagents in a chemical process or could be eliminated from the media used for measurement in a physico-chemical process using ion-exchange resins. The compounds formed due to the spontaneous degradation can also be eliminated with physical processes.

The L-glutaminic acid released from the compound of DNI-Glu*TFA can be preferably neutralized with the addition of glutamate dehydrogenase or glutamate-pyruvate transaminase enzyme. The measurement signals did not reduce despite of the presence of the reagents because the reagents themselves do not have physiological effects, even the signal-to-noise ratio became considerably better. Also, in the case of the use of DNI-Glu base the level of excitatory postsynaptic potential (thereafter EPSP) could be reset to the control level if a reagent was also used beside the so-called "caged reagent" which neutralizes the spontaneously released glutamic acid.

To retain the character of EPSPs is very important, because if the EPSP frequency increases, the basic activity of the cell deviates from the normal level which can lead to the cell death. Using the voltage-clamp method the change of the spontaneous activity of a cell is shown in FIG. 1/A, in which the curve a.) shows the control (normal activity), b.) shows the conditions caused by the spontaneous degradation of the added "caged" compound, curve c.) shows the conditions retained to the control level caused by the addition of the enzyme. Results of several parallel experiments are shown in FIG. 1/B, in which the vertical scale bar shows the frequency of EPSP. In case of the shown experiments due to the addition of DNI-Glu to the perfusion solution the frequency of EPSP increased, then restored after the addition of glutamate dehydrogenase enzyme. The result is similar in case of using glutamate decarboxylate enzyme. In Example 17 it is shown that upon examination of eight parallel samples we found that the addition of enzyme restored the frequency of the potential change to the control level, despite of the fact that the measured DNI-Glu significantly increased the frequency. By the addition of the enzyme the frequency of the EPSP could be retained to the control level and the signal-to-noise ratio of the experiments are increased. The experiments remain in physiological conditions with normal cell functions thus the experiments are more controlled and offer better reproducibility. The used enzyme does not change the cell functions, therefore does not interfere with the measurement.

In the following Table we summarised as examples, which enzymes can be used in case of the release of several biologically active compounds, neurotransmitters and neuroactive amines:

| Released biologically active compound | Enzymes (examples) |
| --- | --- |
| Acetylcholine | Acetylcholine esterase |
| Glutamic acid | Glutamate dehydrogenase |
| Serotonin | Monoamine oxidase |
| Noradrenalin | Monoamine oxidase |
| Dopamin | Monoamine oxidase |
| Anandamid | Fatty acid amide hydrolase (FAAH) |
| GABA (gamma amino butiric acid) | GABA-decarboxylase |

The person skilled in the art can choose the appropriate enzyme from the commercially available enzyme compositions based on the general knowledge and the used circumstances of the experiments. The selection of the suitable reagent, preferably enzyme is the part of the general knowledge of the person skilled in art knowing the releasing biologically active compound. The person skilled in the art selects such a reagent which is not dangerous to the examined cells e.g. neurons and does not alter their physiological state. In case of using DNI-Glu such reagents can be the Glutamate dehydrogenase or the Glutamate decarboxylase enzyme.

In the case of the release of DNA, RNA or fragments thereof, the released biologically active compounds can be neutralized with the use of nuclease enzymes (DNAases or RNAases). In the case of the use of lipid hormones as biologically active compounds the compounds released due to the spontaneous degradation can be neutralized e.g. with the use of Fatty acid dehidrogenase (FAD) enzyme or with enzymes which hydrate the fatty acids, $NAD^+$ kinases, Thiolysis CoA. enzymes.

In the case of the release of peptides peptide-degrading enzymes can also be used. In the case of the release of secondary signal compounds, the $Ca^{2+}$ ions evolved during the spontaneous hydrolysis of a photocleavable compound can be neutralized with the use of $Ca^{2+}$ chelating agents.

Alternatively, we can place an adsorbent in the measuring fluid or the circulation system thereof, which adsorbs partly or completely by a physical or a chemical process the biologically active compound released due to the spontaneous hydrolysis.

In the case of the release of ionic compounds such as amino acids an anionic or cationic ion exchange resin can be placed in the measuring fluid or the fluid can pass through a column filled with an ion exchange resin to absorb the amino acid. Using acidic ion exchange resins the amino acids and the neurotransmitters can also be absorbed. For the absorption of amines or amino acids acidic ion exchange resins containing sulphonic acid groups can be used preferably, while basic ion exchange resins can be used for the absorption of compounds containing carboxyl groups. The selection of the suitable ion exchange resin depends on the properties of the separated compound and the selection is the part of the knowledge of the person skilled in the art. Similarly, solid phase extraction also can be used. The adsorbents for solid extraction are used similarly to the use of ion exchange resins but among these adsorbents we can find suitable types for the absorption of apolar compounds, such as steroids.

The spontaneously released biologically active ingredients can be removed from the measuring media by a biological process. In case the cells or a tissue thereof capable of assimilating the biologically active compounds are used as reagent and placed in the flow of the measuring fluid or in the measuring cell we can avoid the increase of the concentration of the spontaneously released biologically active compound. For example, if hippocampus cells are examined and glutamic acid releases, the measuring fluid passes through a hippocampus cell mass before the inlet of the measuring cell, thus these cells absorb and assimilate the glutamic acid formed in the measuring fluid. Thus, the amount of glutamic acid can not be increased in the measuring fluid. If such a genetically modified cell line is placed which expresses increasingly a protein(s) which helps the assimilation of the active compound, the effect can be improved.

The person skilled in the art easily selects the suitable method and the suitable accessory agent for the neutralisation of the biologically active compounds of the spontaneous degradation from the selection of the above mentioned methods and known reagents.

Particularly, according to the present invention, in the compounds of the general formula (I) the meaning of withdrawing group is a cyano, a nitro, a carboxyl, a formyl group or a halogen atom; the meaning of saturated alkyl group is a straight or branched $C_1$-$C_6$ alkyl groups, e.g. methyl, ethyl, isopropyl or tert. butyl group. The meaning of unsaturated alkyl group is a straight or branched substituted or unsubstituted carbon chain containing one or more isolated or conjugated double or triple bounds. The alkyl groups can have substituents such as halogen atoms, carboxyl groups, primary, secondary or tertiary amino groups. The halogen atom can be e.g. iodo, chloro, bromo or fluoro atom. The meaning of alkoxy group is a group of the formula alkyl-O— in which the alkyl group is as defined above. Such alkoxy groups are e.g. methoxy, ethoxy, n-propoxy, i-propoxy, n-butoxy, 2-oxy malonic acid, 3-dimethylamino-propoxy, 2-dimethylaminoethoxy, 2-dimethylamino-1-methyl-ethoxy, 4-dimethylaminobutoxy, 3-dimethylamino-1-methyl-propoxy groups. Cycloalkyl groups according to the present invention are carbon atoms forming a non-aromatic ring or rings such as cyclopropyl, cyclopentyl or cyclohexyl group. Cycloalkoxy groups are such groups in which the cycloalkyl group is attached to the other part of the compound with an ether type oxygen atom. The cycloalkyl or cycloalkoxy groups can be substituted with e.g. halogen atoms (e.g. I, Cl, Br, F), cyano group, substituted or unsubstituted alkyl, cycloalkyl, alkoxy, cycloalkoxy, or with heterocyclic rings having 5-7 members containing 1-3 hetero atoms in which the hetero atoms can be independently oxygen sulphur or nitrogen. Preferably, the heterocyclic ring is saturated and contains 2 hetero atoms, more preferably the heterocyclic compound is a morfolinyl or piperazinyl group. In the case of compound contains substituted amino groups, these substituents can be alkyl, cycloalkyl or cycloalkoxy groups. These groups are defined above. According to the present invention aryl groups are mono or polycyclic aromatic groups such as phenyl, naphtalenyl, the meaning of hetero aryl groups is an isolated or conjugated cyclic aromatic group containing hetero atom such as pyridyl group. The meaning of amino acid residue according to the present invention is an acid residue of a natural amino acid or a derivative thereof preferably. Natural amino acids are the essential amino acids such as lysine, alanine, proline and further amino acids which have a role in the organ of human being or in an animal, e.g. in the conduction such as gamma-amino-butiric acid or derivatives thereof. In a preferred case the amino acid residue is an acid residue of a neuroactive amino acid which splits from a photocleavable compound due to the light irradiation. Such compound can be the acid residue of glutamic acid, the 4-amino-4-carboxy-1-oxo-but-1yl group, or the acid residue of gamma amino butyric acid (GABA), the 1-oxo-4-amino-butyl group.

The amine residue of a neurotransmitter is derived by removal of one of the hydrogen atoms of the amino group of the neurotransmitter compound. For example the amine residue of dopamine is the 2-(3,4-dihydroxyphenyl)-ethyl-amino group, and the amine residue of the adrenaline and noradrenaline is the (R)-2-(3,4-dihydroxyphenyl)-ethyl-amino, and the amine residue of histamine is the 2-(1H-imidazole-4-yl)-ethyl amino group.

Compounds assumed to be neurotransmitters are the new or known compounds containing at least one amino group which are expected to have neuroactive effect. Such compounds can be tested in a certain stage of the pharmaceutical research with the method according to the present invention.

According to an advantageous embodiment of the present invention the trifluroacetic acid salts of dinitro compounds can be used. The use of dinitro compounds or salts is more preferable from the point of view of testing than the use of mono-nitro compounds, because the excitatory postsynaptic potential (thereafter EPSP) resulted by irradiation is significantly higher using DNI-Glu than using MNI-Glu—shown in FIG. 2—according to the results of our experiments (Example 18). These test results are shown in FIG. 2/A, where the horizontal scale bar represents 50 ms of time unit and the vertical scale bar represents 2 mV of voltage. The FIG. 2/B shows that the $Ca^{2+}$ transient sign as a response of the photolysis is also significantly higher in case of using DNI-Glu than in case of using MNI-Glu. A further advantage of the use of di-nitro compounds is that they give higher excitatory postsynaptic potential (thereafter EPSP) and $Ca^{2+}$ transient signs independently from the wavelengths of the used light than the corresponding mono-nitro derivatives. The signal magnitudes depending on the used light wavelengths are shown in FIG. 3. (FIG. 3/A—EPSP; FIG. 3/B $Ca^{2+}$ transient sign.)

The fact that the compounds of the general formula (I) can be used in a trifluoroacetic acid salt form is surprising because the person skilled in the art would expect that the release of the acid compounds such as trifluoroacetic acid of the salt form should interfere the tests.

According to the most advantageous embodiment of the present invention TFA salts of DNI derivatives are used as "caged" compounds in such a way that a reagent is also added to the measuring fluid, which neutralises the spontaneously released biologically active compounds.

Another aspect of the present invention is a process for one or multi-photon irradiation tests, preferably a two-photon irradiation test characterized in that the photocleavable compound, preferably a compound according to the general formula (I) is dissolved in the measuring fluid and a reagent is added which neutralizes the biologically active compounds resulted from the spontaneous degradation, then the natural fluid of the sample is changed to this solution, and the test is carried out using this sample according to a known manner using the equipments according to the state of the art.

As a measuring fluid Ringer solution or ACSF solution (Artificial CerebroSpinal Fluid), or any other solution having a suitable composition can be used. The selection of the measuring fluid is the part of the knowledge of the person skilled in the art.

Particularly, in the case of observation of nervous cells and the formed biological active amino acid, the compound of the general formula (I) or a salt thereof is dissolved in Artificial CerebroSpinal Fluid (ACSF) and a calculated amount of reagent which neutralizes the amino acid formed by spontaneous decomposition. The reagent is preferably an enzyme.

The amount of the reagent needed can be easily calculated depending on the photocleavable compound and the reagent as follows:

The photocleavable compound is dissolved in Artificial CerebroSpinal Fluid (ACSF) fluid in an amount which is used in the tests. The composition of ACSF is as follows:

| Compound | Concentration | g/1 l solution |
|---|---|---|
| NaCl | 126 mM | 7.363 |
| KCl | 2.5 mM | 0.1864 |
| $CaCl_2$ | 2 mM | 0.29404 |
| $MgCl_2$ | 2 mM | 0.4066 |
| $NaH_2PO_4$ | 1.25 mM | 0.17249 |
| (Glucose) (anhydrous) | 10 mM | 1.8016 |
| $NaHCO_3$ | 26 mM | 2.184 |

The obtained solution is sampled at start and 48 hours later. The amount of the active ingredient is determined by high pressure liquid chromatography (HPLC), e.g. in case of DNI derivatives from the increase of 4-methoxy-5,7-dinitroindoline which is a degradation product of DNI derivatives. We calculate the amount of the amino acid release during a usual one- or multi-photon test, then knowing the activity of an enzyme product we add such an amount of the enzyme to the measuring fluid, which is capable of deactivating the amino acid formed by the spontaneous decomposition.

A further aspect of the present invention is a composition comprising compounds of the general formula (I) or a salt thereof and a reagent which neutralizes the biologically active compounds of the spontaneous degradation of the compounds of the general formula (I) and further accessory agents if necessary. The useful accessory agents are such inert compounds, which are generally used in the pharmaceutical industry. Types, properties and uses of these accessory agents are shown particularly in the Handbook of Pharmaceutical Excipients (Fifth Edition, edited by Raymond C Rowe, Paul J Sheskey and Siân C Owen Published 2006).

The person skilled in the art can prepare this composition according to the processes generally used in the pharmaceutical industry. Such methods are shown particularly in the PHARMACEUTICAL MANUFACTURING HANDBOOK (SHAYNE COX GAD, PH. D., D.A.B.T.; 2008 by John Wiley & Sons, Inc).

We found that the tests can be carried out significantly easier if the components are dissolved as a premix in the measurement media, preferably in a solution of artificial cerebrospinal fluid (ACSF). In this case the measuring time shortens because it is not necessary to measure and dissolve two compounds. A further, advantage of the use of premixes is that the rate of the "caged" compound and the reagent is constant therefore the deviation of the parallel tests can be reduced. Furthermore the accuracy of the tests is increased because larger amounts have to be measured. As mentioned above, the lack of a reagent which neutralizes the biologically active compounds evolved during the tests can falsify the test results and can even result in the sensibilization or the death of the cells, thus the test can become impossible.

According to the present invention, the term "premixes" means a mixture which contains the photochemically cleavable active ingredient and the reagent capable of neutralizing the biologically active compounds formed by spontaneous degradation thereof together or separately which is used mixed with further accessory agents. The premixes can be either mixtures containing only the caged compound or only the reagent capable of neutralizing the biologically active ingredients formed by degradation thereof with accessory agents, or mixtures containing the photochemically active compound with the reagent together. The premixes can be prepared in a solid or liquid form, preferably in solid form. The premix can be a powder mixture containing additional, but at least one accessory agent(s) beyond the photochemically cleavable compound and the reagent, which neutralizes biologically active compounds, e.g. amino acids formed by spontaneous degradation. Such accessory agents can be organic or inorganic compounds, such as sodium chloride, potassium chloride, calcium chloride, magnesium chloride, sodium dihydrogen phosphate, glucose, nicotinamide-adenine-dinucleotide-phosphate (NADP), disodium salt.

The premixes can be prepared by mixing the photochemically active ingredient and the reagent with the accessory agents in a ratio based on the above-mentioned measurements and calculations and the mixture is homogenized. The mixing is carried out in a dry place under nitrogen atmosphere if necessary. The mixture is stored frozen at −20° C. if necessary.

In the case of the premix is a powder mixture, it can be compressed into tablets, or filled into capsules or can be formed as a dose unit in a different form. We may formulate the photochemically active compound and the reagent separately and the obtained powder mixtures can be formed to dose units.

A further aspect of the present invention is a KIT in which the photochemically active ingredient and the reagent are formulated separately and placed in a common packing unit. Such packing unit can be a box, blister, capsule etc.

Further embodiments of the present invention are the trifluoroacetic acid salts of the compounds of the general formula (I) which can be used in one- or multi-photon irradiation experiments and in which $R^1$ stands for a nitro group; $R^2$ stands for a hydrogen or bromo atom, or straight or branched substituted or unsubstituted alkoxy, cycloalkoxy, preferably $C_1$-$C_6$ alkoxy group, substituted with an unsubstituted amino group, or an amino group substituted with a $C_1$-$C_6$ alkyl group or cycloalkyl group, or two identical or different $C_1$-$C_6$ alkyl groups, aryl group, heteroaryl group or cycloalkyl group; or substituted or unsubstituted aryl group;

$R^3$ and $R^4$ stand for a hydrogen atom; $R^5$ is an acid residue of an amino acid or a group of the general formula (II) in which the nitrogen atom and the attached $R^6$ and $R^7$ substituents together stand for an amine residue of an amino acid and X stands for an oxygen or sulphur atom.

Each of these compounds is cleavable in a two-photon irradiation process. The two-photon irradiation process has advantages against the one-photon process, because it allows the neurotransmitters be free adjacent to the receptors even in a very small volume. The further advantage of the small excitation volume is that the laser beam does not destruct or very slightly destructs the dendrites. A further advantage is that in case of the two-photon process the wavelength of the used laser beam is near to the infrared range against the one photon process, which uses light in the UV range for irradiation. Combining the two-photon excitation with the two-photon imaging process several brain processes can be modelled deep in the tissue beside the least possible side effects.

Using the two-photon irradiation process the location of excitation can be set very precisely during the measurement, thus it allows the neurobiological examination of neurons. In the case of the experimental setup shown in FIG. 5/A 20 irradiation points were located along the dendrite then the experiment was carried out according to the process described in Example 16 with the difference that iDMPO-DNI-GABA*2 TFA salt (2.5 mM) was used as "caged" compound. We measured the replies caused by stimulation of each point and show them with some example curves. These curves can be seen in FIG. 5/B. Repeating these experiments several times it could be shown that the receptor density was different along the soma. As a result of the stimulations of several experiments the average of the signals shows differences as demonstrated in FIG. 5/C. Surprisingly, the use of TFA salts of the "caged" compounds enables the examination of the receptor density and the neurobiological structure of the neuron.

The most advantageous embodiment of the present invention relates to the trifluoroacetic acid salts of the compounds of the general formula (I) and the process for the preparation thereof, in which $R^1$ stands for a nitro group; $R^2$ stands for a hydrogen or bromo atom, or dimethylamino-ethoxy group, dimethylamino-propoxy, isomers of dimethylamino-isopropoxy group (—O—CH($CH_3$)$CH_2$—N($CH_3$)$_2$ and O—$CH_2$—CH($CH_3$)—N($CH_3$)$_2$ groups), dimethylamino-isobutoxy group (O—$CH_2$—CH($CH_3$)—$CH_2$— N($CH_3$)$_2$; or substituted or unsubstituted aryl group; $R^3$ and $R^4$ stand for a hydrogen atom; $R^5$ stands for an acid residue of L-Glutamic acid, GABA or Glycin, or a group of the general formula (II) in which the nitrogen atom and the attached $R^6$ and $R^7$ substituents together stand for an amine residue of L-Glutamic acid, GABA or Glycin and X stands for an oxygen or sulphur atom.

According to the advantageous embodiment in the trifluoroacetic acid salt of the compound of the general formula (I)

$R^5$ is an acid residue of an amino acid or $R^5$ is a group of the general formula (II) in which the nitrogen atom and the attached $R^6$ and $R^7$ substituents together stand for an amine residue of a neurotransmitter or a compound assumed to be a neurotransmitter and X stands for an oxygen or sulphur atom.

The advantage of these trifluoroacetic acid salts compared to the bases and other salts are that they are more stable, less photosensitive and hygroscopic and it is easy to prepare and purify them. Our tests proved that the salt forms of the compounds according to the general formula (I) are less hygroscopic in salt form than the base. We measured the weight increase of MNI-Glubase and its salts with hydrochloric and trifluoroacetic acid at 25° C. 50% relative humidity. After 72 hours storage the weight of the base increased by 20%, the weight of the HCl salt increased by 13.6%, meanwhile the increase of the weight of the trifluoroacetic acid salt was only 4%.

Further advantages of salts are that they are easy to prepare, purify and they are more stable than bases or other salts.

According to the most advantageous embodiment of the present invention the new TFA salts of dinitro-indoline derivatives (caged compounds) make it possible that due to their better solubility and stability—unlike similar derivatives known from the prior art—they can be used in two-photon irradiation experiments beside the addition of the suitable enzyme into the measurement fluid. Thus, a significantly higher quantum yield can be exploited, which characterizes the DNI derivatives.

We found surprisingly that the compounds of the general formula (I), in which $R^1$ stands for a nitro group; $R^2$ stands for a $C_1$-$C_6$ alkoxy group, substituted with an unsubstituted amino group, or with an amino group substituted with a $C_1$-$C_6$ alkyl group or cycloalkyl group, or two identical or different $C_1$-$C_6$ alkyl groups, have very advantageous properties. Unlike the dinitro-indoline type caged compounds known from the prior art these compounds surprisingly remain in the solution after the cleave of the caged compound because they are soluble in the measuring fluid. This fact ensures that these compounds can be completely removed with the change of the measuring liquid, therefore they do not disturb the following measurements.

Another aspect of the present invention is a process for the preparation of trifluoroacetic acid salts of the compounds of the general formula (I) with trifluoroacetic acid in which $R^1$ stands for a nitro group; $R^2$ stands for a hydrogen or bromo atom, or a straight or branched, substituted or unsubstituted alkoxy, cycloalkoxy, preferably $C_1$-$C_6$ alkoxy group, wherein the substituent is an unsubstituted amino group, or an amino group substituted with a $C_1$-$C_6$ alkyl group or cycloalkyl group, or two identical or different $C_1$-$C_6$ alkyl groups, aryl group, heteroaryl group or cycloalkyl group; or substituted or unsubstituted aryl group; $R^3$ and $R^4$ stand for a hydrogen atom; $R^5$ is an acid residue of an amino acid or a group of the general formula (II), in which the nitrogen atom and the attached $R^6$ and $R^7$ substituents together stand for an amine residue of an amino acid and X stands for an oxygen or sulphur atom, in such a way that the trifluoroacetic acid or a solution thereof is added to a solution of the compounds of the general formula (I) and the formed salt is separated. According to a preferred embodiment of the present invention the trifluoroacetic acid or the solution thereof is added to the reaction mixture of the preparation of the compound of the general formula (I) and the salt is separated from this solution. The separation of the salt can be carried out by filtration or working up of the evaporated reaction mixture. The salts can be separated from the solution so that such solution is added to the mixture which precipitates the salt, but we can separate the product by cooling the mixture.

The crude salt can be recrystallised or transformed into a base form if necessary. The advantage of this process is that the chromatographic purification is not necessary during the preparation of the product.

An advantage of the present invention is that in the course of one- or multi-photon excitation tests it permits the neutralisation of the spontaneously formed amino acids which disturb the tests.

The examined nervous cell is protected from the harmful effect of an increased concentration of the hydrolysed products.

The composition according to the present invention containing a compound of the general formula (I) and a reagent for neutralizing the spontaneously formed amino acids enables a smaller deviation in series of tests and facilitates the measuring.

The salts of the compounds of the general formula (I) with trifluoroacetic acid can be easily prepared, purified and they are more stable than the corresponding bases and the other salts.

BRIEF DESCRIPTION OF DRAWINGS

FIG. 5A—Shows the experimental arrangement of the neurobiological examination of a neuron with a two-photon irradiation method using iDMPO-DNI-GABA*2 TFA as caged compound.

FIG. 5B—Shows the responses to stimulation rate of the neurobiological examination of a neuron with a two-photon irradiation method using iDMPO-DNI-GABA*2 TFA as caged compound.

Figure 1A:
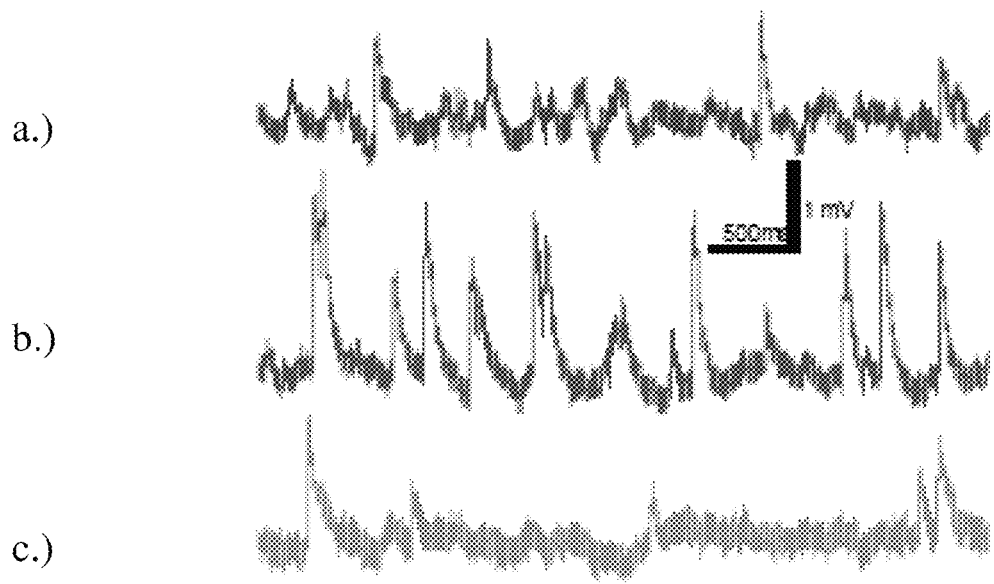
FIG. 1A—Shows the change of the spontaneous activity of the cell due to addition of a caged compound and an enzyme in a voltage-clamp test according to Example 17.

The present invention is shown particularly in the examples below without the limitation of the scope of the present invention to these examples.

EXAMPLE 1

Process for the preparation of trifluoroacetic acid salt of 2-amino-5-(4'-methoxy-5',7'-dinitro-2',3'-dihydro-indol-1'-yl)-5-oxo-pentanoic acid

[DNI-Glu*TFA]

In 1.8 ml of trifluoroacetic acid (TFA) 0.1 g (0.19 mmole) of [2-(benzyl-oxy-carbonyl-amino)-5-(4'-methoxy-5',7'-dinitro-2',3'-dihydro-indol-1'-yl)-5-oxo-pentanoic acid tert-butylester] was dissolved at 0° C., than stirred at room temperature for 92 hours. Then 2×2 ml of methanol were added and the mixture was evaporated. To the oily residue 5 ml of diethylether was added, the precipitated crystals are filtered and dried in an exicator. Thus the product is 0.05 g of a brown, solid title compound.

The yield is 54%, purity is 99.8% (HPLC), LC-MS: 368. Melting point: 146-148° C.; The crystalline product due to the humidity of the air adsorbs crystal water at room temperature.

The elementary analysis of the product thus produced is as follows:

| | Formula | Mole weight | Calculated value: | Measured value: |
|---|---|---|---|---|
| DNI-GLU*TFA*$H_2O$ | $C_{16}H_{19}F_3N_4O_{11}$ | 500.34 | C, 38.41; H, 3.83; N, 11.20; | C, 39.87 H, 3.81 N, 11.85 |

NMR Spectra:

| Serial No. | Chemical deviation (ppm) | Attachment (Hz) | Type |
|---|---|---|---|
| 1 | 2.05 (m) | 6.2; 1.7 | $CH_2$ |
| 2 | 2.73 (d.q) | 7.0; 2.4 | CO—$CH_2$ |
| 3 | 3.40 (t) | 7.9 | Ar—$CH_2$ |
| 4 | 3.93 (s) | — | O—$CH_3$ |
| 5 | 4.01 (s) | — | CO—CH |
| 6 | 4.29 (m) | 7.9; 2.0 | N—$CH_2$ |
| 7 | 8.32 (d) | 9.0 | Ar—H |

EXAMPLE 2

Process for the preparation of di-trifluoroacetic acid salt of 4-amino-1-(4'-dimethylamino-ethoxy-5',7'-dinitro-2',3'-dihydro-indol-1'-yl)-1-oxo-butane [DMEO-DNI-GABA*2TFA]

In a 3:1 mixture of 200 ml of toluene and methanol 6.6 g (0.123 mole) of sodium methylate were dissolved, then a solution of 15 g of (0.1125 mole) 4-hydroxyindole in 250 ml of a 3:2 mixture of toluene and methanol at 60° C. was added dropwise to the solution, then the mixture was stirred for half an hour at this temperature. Then 14.5 g (0.135 mole) dimethyl-amino-ethyl-chloride were dissolved in 14.5 ml of toluene at 60° C. and stirred for further 5 hours at this temperature. During this time the 4-hydroxy-indol completely transformed.

Then 300 ml of ethyl acetate were added to the reaction mixture, then the mixture was filtered through Perlite. The solution was extracted with saturated sodium hydrogen carbonate solution, following the separation it was extracted with 3×150 ml of water, dried on magnesium sulphate, then evaporated.

The product thus obtained is 10.82 g (51%) pale brown oil of 4-dimethylamino-ethoxy-indole (DMEO-Indole).

The product of 10.82 g (52.9 mmoles) of DMEO-Indole obtained in the previous reaction step was dissolved in 50 ml of acetic acid, then 3.32 g of (52.9 mmoles) of sodium cyanoborohydride were added in portions at a temperature between 10-15° C. The cooling was stopped and the reaction mixture was allowed to heat to 20° C., then stirred for 3 hours at this temperature. The completion of the reaction was checked with thin layer chromatography (TLC). The reaction mixture was cooled at 10° C. under stirring. The pH of the mixture was adjusted to pH 8 by addition of 150 ml of 20% of sodium hydroxide solution, then the mixture was extracted with 3×150 ml of ethyl acetate. The unified organic phase was dried on magnesium sulphate, filtered and evaporated. The thus obtained 8.5 g (79%) of pale brown oil is 4-dimethylamino-ethoxy-2,3-dihydro-indole (DMEO-Indoline).

In 50 ml of ethyl acetate 3.39 g (16.7 mmoles) of 4-(tert.butoxycarbonyl-amino)-butanoic acid (BOC-GABA) were dissolved, and 4.8 ml of diisopropyl-ethylamine were added to the mixture, then cooled at 15° C. and 3.8 ml (21.4 mmoles) of N-ethyl-dimethyl-amino-propyl-carbodiimide were added. The reaction temperature was allowed to increase to 20° C., then a solution of 3.0 g (23.0 mmoles) DMEO-indoline in 70 ml of ethyl-acetate was added dropwise to the solution. Following the addition the reaction mixture was stirred at 20° C. for 1 hour. The reaction was fully completed. The pH of the mixture was adjusted to pH 4 with addition of 25 ml of 1M hydrochloric acid, then the mixture was separated, the organic phase was washed with 15 ml of saturated sodium hydrogen carbonate solution.

The organic layer is dried on magnesium sulphate, filtered and evaporated. The given crude product was recrystallised from ethanol. The product thus obtained is 4.7 g (85%) white crystalline of 4-terc.butoxycarbonyl-amino-1-(4'-dimethyl-amino-ethoxy-2',3'-dihydro-indol-1'-yl)-1-oxo-buthane [DMEO-I-Boc-GABA].

4.7 g of DMEO-I-Boc-GABA were added to 15 ml of trifluoroacetic acid under stirring and the stirring was continued for one additional hour. The mixture was evaporated, then 3*10 ml of methanol were added and evaporated to eliminate the TFA completely. The thus obtained 7.63 g of oil was di-trifluoroacetic acid salt of 4-amino-1-(4'-dimethylamino-ethoxy-2',3'-dihydro-indol-1'-yl)-1-oxo-butane (DMEO-I-GABA*2TFA).

Under stirring 4 g (7.7 mmoles) of DMEO-I-GABA*2TFA were dissolved in 400 ml of trifluoroacetic acid, then 19.63 g (230 mmoles) of sodium nitrate were added in portions at 10° C. The reaction mixture was allowed to warm up to 20° C. It was stirred for an additional hour at this temperature. The completion of the reaction was checked with HPLC method.

To the reaction mixture 800 ml of dichloromethane were added and the precipitated inorganic salts weighing 30 g were filtered off, the filtrate was evaporated and dissolved in 30 ml of dioxane, the separated inorganic salts were filtered and the solution was evaporated. The thus obtained brown oil was purified by preparative HPLC. The used eluent was aqueous acetonitrile containing 0.1% of TFA, which provided that the product remained in TFA salt form. The product is 0.43 g of yellow crystalline di-trifluoroacetic salt of 4-amino-1-(4'-dimethylamino-ethoxy-5',7'-dinitro-2',3'-dihydro-indol-1'-yl)-1-oxo-butane [DMEO-DNI-GABA*2TFA]*2H$_2$O.

|  | Formula: | Mole weight | Calculated value: | Obtained value: |
|---|---|---|---|---|
| DMEO-DNI-GABA*2TFA*H$_2$O | C$_{20}$H$_{27}$F$_6$N$_5$O$_{11}$ | 627.45 | C. 38.28; H. 4.34; N. 11.16; | C. 39.97 H. 4.81 N. 9.32 |

EXAMPLE 3

Process for the preparation of di-trifluoroacetic acid salt of 4-amino-1-(4'-dimethylamino-isopropoxy-5', 7'-dinitro-2',3'-dihydro-indol-1'-yl)-1-oxo-butane [iDMPO-DNI-GABA*2TFA]

The compound of 4-amino-1-(4'-dimethylamino-isopropoxy-5',7'-dinitro-2',3'-dihydro-indol-1-yl)-1-oxo-butane [iDMPO-DNI-GABA*2TFA] was prepared according to the process of the preparation of DMEO-I-GABA*2TFA using hydroxyindole as starting material.

In 35 ml of acetonitrile 3.5 g (6.54 mmoles) of iDMPO-I-GABA*2TFA were dissolved, then 1.73 g (13.5 mol) nitronium-tetrafluoro-borate is added at 10° C. mixture was allowed to warm up at 20° C. The mixture was stirred at that temperature for 3 hours. The reaction was checked with HPLC. To the reaction mixture 20 g of sodium hydrogen carbonate were added and stirred for 0.5 hours, then it was stirred with 20 g of magnesium sulphate for further 0.5 hours, filtered and evaporated. The obtained product is 5.52 g crude brown oil, which was purified by HPLC (eluent: aqueous acetonitrile containing 0.1% of TFA). The thus obtained 0.600 g yellowish brown waxy like oil is the di-trifluoroacetic acid salt of 4-amino-1-(4'-dimethylamino-isopropoxy-5',7'-dinitro-2',3'-dihydro-indol-1'-yl)-1-oxo-butane [iDMPO-DNI-GABA*2TFA].

EXAMPLE 4

Process for the preparation of trifluoroacetic acid salt of (S)-4-amino-5-(4'-methoxy-7'-nitro-2',3'-dihydro-indol-1'-yl)-5-oxo-pentanoic acid [MNI-Ulg*TFA]

The used process is an analogue process to the preparation of DMEO-MNI-Glu*2TFA, in which methoxy-indoline is used as starting material. For the coupling L-glutamic acid N-[(1,1-dimethyl-ethoxy)carbonyl]-5-(1,1-dimethyl-ethyl) ester was used. The obtained yellow crystals are the trifluoroacetic salt of (S)-4-amino-5-(4'-methoxy-7'-nitro-2',3'-dihydro-indol-1'-yl)-5-oxo-pentanoic acid [MNI-Ulg*TFA*H2O]

|  | Formula: | Mole weight | Calculated value | Obtained value: |
|---|---|---|---|---|
| MNI-Ulg*TFA*H$_2$O | C$_{16}$H$_{20}$F$_3$N$_3$O$_9$ | 455.34 | C. 42.20; H. 4.43; N. 9.23; | C. 43.11 H. 4.27 N. 8.59 |

EXAMPLE 5

Process for the preparation of trifluoroacetic salt of 2-amino-1-(7'-nitro-2',3'-dihydro-indol-1'-yl)-1-oxo-ethane [MNI-Gly*TFA]

The used process is analogue to the preparation of DMEO-MNI-Glu*2TFA, in which methoxy-indoline is used as starting material. For the coupling N-[(1,1-dimethyl-ethoxy)carbonyl]glycine was used.

The thus obtained 90 mg of yellow crystalline product is the trifluoroacetic acid salt of 2-amino-1-(7'-nitro-2',3'-dihydro-indol-1'-yl)-1-oxo-ethane [MNI-Gly*TFA].

EXAMPLE 6

The Spontaneous Hydrolysis of DNI-Glu*TFA

For this experiment artificial cerebrospinalis fluidum (ACSF) was used, which composition is shown in the following table:

| Compound | Concentration | g/1 l solution |
| --- | --- | --- |
| NaCl | 126 mM | 7.363 |
| KCl | 2.5 mM | 0.1864 |
| $CaCl_2$ | 2 mM | 0.29404 |
| $MgCl_2$ | 2 mM | 0.4066 |
| $NaH_2PO_4$ | 1.25 mM | 0.17249 |
| Glucose(anhydrous) | 10 mM | 1.8016 |
| $NaHCO_3$ | 26 mM | 2.184 |

10 ml of ACFS solution containing 0.06 mg/ml of DNI-Glu*TFA was stored at 32° C. The solution was sampled at the beginning of the storage and 48 hours later and 4-methoxy-5,7-dinitro-2,3-dihydro-1H-indole was identified from the hydrolysis products by using LCMS method. The compound was identified by the peak of its molecule weight at 240. The sample taken after 48 hours was measured with HPLC equipment. Without correction 46.7% of DNI-Glu*TFA hydrolysed.

EXAMPLE 7

Neutralisation of Glutamic Acid Formed from the Degradation of DNI-Glu*TFA Spontaneous Hydrolysis Using Glutamic Acid-Pyruvic Acid Transaminase Enzyme Calculation of the Necessary Amount of Enzyme:

Results of Example 6 shows that the speed of the formation of the glutamic acid is 1 μmole/minute in 12 ml of ACSF, which is usually used in mono- or two-photon irradiation experiments.

For the transformation of the forming glutamic acid in 12 ml of ACSF solution containing 13.5 mg of DNI-Glu*TFA to α-ketoglutaric acid one unit glutamic acid-pyrucic acid transaminase is required. (Sigma cat. No.: G8255). Thus, before the test one unit of glutamic acid-pyrucic acid transaminase was added to the ACSF solution.

EXAMPLE 8

Neutralisation of Glutamic Acid Formed from the Degradation of DNI-Glu*TFA Spontaneous Hydrolysis Using L-Glutamic Acid Dehydrogenase (Sigma G2626) and NADP (β-Nicotinamide Adenine Dinucleotide Phosphate, /Sigma N5755/)

Calculation of the Necessary Amount of Enzyme:

Results of Example 6 shows that the speed of the formation of the glutamic acid is 1 μmole/minute in 12 ml of ACSF, which is usually used in mono- or two-photon irradiation experiments.

We proceed according to Example 7 with the difference that instead of glutamic acid-pyrucic acid transaminase enzyme L-glutamic acid dehydrogenase enzyme and NADP (β-Nicotinamide adenine dinucleotide phosphate) are used.

To 12 ml of ACSF solution DNI-Glu*TFA is added in an amount which results in a concentration of 2.5 mM of DNI-Glu*TFA in the solution and to this solution 2 units of L-glutamic acid dehydrogenase enzyme (2.1 μl) and 12 μl NADP stock-solution (NADP 200 mM) are added.

EXAMPLE 9

Composition Containing DNI-Glu*TFA, L-Glutamic Acid Dehydrogenase Enzyme and β-Nicotinamide Adenine Dinucleotide Phosphate (NADP)

In dry condition and nitrogen atmosphere 14.5 mg DNI-Glu*TFA were measured into a glass container, then 1.8 mg of NADP and 1 unit of glutamic acid dehydrogenase enzyme (2.1 μl glycerol containing solution) were added in a manner that the solution containing glycerol was layered onto the wall of the glass touching at all not or only minimally with the DNI-Glu*TFA. The container was closed under nitrogen. The composition was stored in a refrigerator. The product was used in this form.

EXAMPLE 10

Process for the preparation of di-trifluoroacetic acid salt of 2-amino-1-(4'-dimethylamino-isobutoxy-5', 7'-dinitro-2',3'-dihydro-indol-1'-yl)-5-oxo-pentanoic [iDMBO-DNI-Glu*2TFA]

In a 3:1 mixture of 160 ml of toluene and methanol 18.9 g (225 mmoles) of sodium methylate were dissolved, then a solution of 20 g of (15 mmoles) 4-hydroxyindole in 200 ml of a 3:2 mixture of toluene and methanol at 60° C. was added dropwise to the solution, then the mixture was stirred for half an hour at this temperature. Then a 50% solution of 50 g (375 mmoles) dimethyl-amino-isobutyl-chloride in xylene was added dropwise to the solution and stirred at 60° C. for further 25 hours at this temperature. During this time the starting compound was completely transformed. The mixture was cooled to 15° C., then 300 ml of ethyl acetate were added to the reaction mixture, then the mixture was filtered through Perlite. The solution was extracted with saturated sodium hydrogen carbonate solution, following the separation it was extracted with 3×150 ml of water, dried on magnesium sulphate, then evaporated. The product thus obtained is 24.7 g (86%) pale brown crystalline [iDMBO-Indole].

The product of 24 g (103.9 mmoles) of iDMBO-Indole obtained in the previous reaction step was dissolved in 130 ml of acetic acid, then 6.46 g (103.9 mmoles) of sodium cyanoborohydride were added in portions at a temperature 10° C., then reacted for further 3 hours. The completion of the reaction was checked with thin layer chromatography (TLC). After the extinction of the starting compound the reaction mixture was cooled at 10° C. under stirring. The pH of the mixture was adjusted to pH 8 by addition of 300 ml of 20% of sodium hydroxide solution, and then the mixture was extracted with 3×150 ml of dichloromethane, dried on magnesium sulphate, filtered and evaporated.

The thus obtained 19.2 g of pale brown oil is 4-dimethylamino-isobutoxy-2,3-dihydro-indole (iDMBO-Indoline).

In 60 ml of ethyl acetate 7.28 g (24 mmoles) of BOC-Glu-(OH)-OtBu were dissolved, and 4.3 ml of diisopropyl-ethylamine were added to the mixture, then cooled at 15° C. and 4 ml (22. mmoles) of N-ethyl-dimethyl-amino-propyl-carbodiimide were added. The reaction temperature was allowed to increase to 20° C., then a solution of 5.0 g (21.0 mmoles) iDMBO-indoline in 60 ml of ethyl-acetate was added dropwise to the solution. Following the addition the reaction mixture was stirred at 20° C. for 1 hour after completion of the reaction (checked with HPLC). The mixture is cooled to 10° C., then the pH of the mixture was adjusted to pH 4 with the addition of 30 ml of 1M hydrochloric acid, then the mixture was separated, the organic phase was washed with 15 ml of saturated sodium hydrogen carbonate solution to pH 8, then separated. The organic layer was dried on magnesium sulphate, filtered and evaporated.

The product obtained was 10.5 g of pale brown oily crystalline [iDMBO-I-Boc-Glu].

In 50 ml of acetonitrile 5 g (9.62 mmoles) of iDMPO-I-BOC-Glu were dissolved, then 3.8 g (28.8 mmol) of nitronium-tetrafluoro-borate were added at 10° C. The mixture was stirred at 20° C. for additional 17 hours, then further 0.69 g (0.00481 mol) of nitronium-tetrafluoro-borate was added to complete the reaction. Thus the reaction was completely finished. To the reaction mixture 9.87 g of sodium hydrogen carbonate and 50 ml of acetonitrile were added and dried with magnesium sulphate and evaporated. The product was purified with HPLC. The eluent used for purification contained trifluoracetic acid to ensure the formation of trifluoracetic acid salt of the product, thus after the purification 0.6 g of iDMBO-DNI-Glu*2TFA was obtained.

$^1$H-NMR (iDMBO-DNI-Glu*2TFA)

|   | Chemical deviation (ppm) | Type |
|---|---|---|
| 1 | 1.07 (d) | —CH$_3$ |
| 2 | 2.05 (m) | CO—CH$_2$ |
| 3 | 2.45 (m) | —CH— |
| 4 | 2.80 (d) | N—CH$_3$ |
| 5 | 3.11; 3.21. (d.t) | —N—CH$_2$ |
| 6 | 3.40 (t) | Ar—CH$_2$ |
| 7 | 3.93 (m) | —CH— |
| 8 | 4.18 (d) | O—CH$_2$ |
| 9 | 4.32 (t) | N—CH$_2$ |
| 10 | 8.30 (s) | Ar—H |
| 11 | 9.7 (b) | —COOH |

EXAMPLE 11

Process for the preparation of di-trifluoroacetic acid salt of 2-amino-1-(4'-dimethylamino-isopropoxy-5', 7'-dinitro-2',3'-dihydro-indol-1'-yl)-5-oxo-pentanoic [iDMPO-DNI-Glu*2TFA]

The used process is analogue to the preparation of iDMBO-DNI-Glu*2TFA, in which 4-hydroxy-indole is used as starting material. For the alkylation reaction dimethylamino-isopropyl chloride was used. The obtained 81 mg of yellow oil product is the trifluoroacetic acid salt of 2-amino-1-(4'-dimethylamino-isopropoxy-5',7'-dinitro-2',3'-dihydro-indol-1'-yl)-5-oxo-pentanoic [iDMPO-DNI-Glu*2TFA]

| MS (iDMPO-DNI-Glu) Molecular formula | exact weight | (m/z)$^-$ |
|---|---|---|
| C18H25N5O8 | 439.17 | 438 |

EXAMPLE 12

Process for the preparation of di-trifluoroacetic acid salt of 4-amino-1-(4'-dimethylamino-isobutoxy-5', 7'-dinitro-2',3'-dihydro-indol-1'-yl)-1-oxo-butane [iDMBO-DNI-GABA*2TFA]

The used process is an analogue process to the preparation of iDMBO-DNI-Glu*2TFA. For the coupling dimethylamino-isobutyl chloride was used. The obtained 90 mg of yellow-brown oil is the trifluoroacetic salt of 4-amino-1-(4'-dimethylamino-ethoxy-5',7'-dinitro-2',3'-dihydro-indol-1'-yl)-1-oxo-buthane [iDMBO-DNI-GABA*2TFA]

$^1$H-NMR (iDMBO-DNI-GABA*2TFA):

|   | Chemical deviation (ppm) | Type |
|---|---|---|
| 1 | 1.07 (d) | —CH$_3$ |
| 2 | 1.62 (t) | CO—CH$_2$ |
| 3 | 1.88 (m) | —CH$_2$— |
| 4 | 2.38 (m) | —CH— |
| 5 | 2.82 (d) | —N—CH$_3$ |
| 6 | 3.07; 3.2 (d.t) | N—CH$_2$ |
| 7 | 3.40 (t) | Ar—CH$_2$ |
| 8 | 4.18 (d) | O—CH$_2$ |
| 9 | 4.31 (t) | N—CH$_2$ |
| 10 | 7.87 (b) | NH$_2$ |
| 11 | 8.37 (s) | Ar—H |

EXAMPLE 13

Process for the preparation of di-trifluoroacetic acid salt of 2-amino-1-(4'-dimethylamino-ethoxy-5',7'-dinitro-2',3'-dihydro-indol-1'-yl)-1-oxo-ethan [iDMBO-DNI-Gly*2TFA]

The used process is an analogue process to the preparation of iDMBO-DNI-Glu*2TFA. For the coupling N-tert-butoxy-2-amino acetic acid (BOC-GLYCIN) was used. The obtained 1.3 g of yellow oil is the trifluoroacetic salt of 2-amino-1-(4'-dimethylamino-ethoxy-5',7'-dinitro-2',3'-dihydro-indol-1'-yl)-1-oxo-ethane [iDMBO-DNI-Gly*2TFA]

$^1$H-NMR (iDMBO-DNI-Gly*2TFA):

|   | Chemical deviation (ppm) | Type |
|---|---|---|
| 1 | 1.08 (d) | —CH$_3$ |
| 2 | 2.45 (m) | —CH— |
| 3 | 2.82 (d) | —N—CH$_3$ |
| 4 | 3.07; 3.19 (d.t) | N—CH$_2$— |
| 5 | 3.42 (t) | —Ar—CH$_2$ |
| 6 | 4.18 (s) | N—CH$_2$ |
| 7 | 4.22 (d) | O—CH$_2$ |
| 8 | 4.31 (t) | N—CH$_2$ |
| 9 | 8.39 (b) | NH$_2$ |
| 10 | 8.41 (s) | Ar—H |

EXAMPLE 14

Process for the preparation of trifluoroacetic acid salt of 4-amino-1-(4'-bromo-5',7'-dinitro-2',3'-dihydro-indol-1'-yl)-1-oxo-butane [Br-DNI-GABA*TFA]

The used process is an analogue process to the preparation of iDMBO-DNI-Glu*2TFA, in which 4-bromo-indole is used as starting material. The obtained 130 mg of yellow crystals is the trifluoroacetic salt of 4-amino-1-(4'-bromo-5',7'-dinitro-2',3'-dihydro-indol-1'-yl)-1-oxo-butane [Br-DNI-GABA*TFA]

$^1$H-NMR (Br-DNI-GABA*TFA):

|   | Chemical deviation (ppm) | Type |
|---|---|---|
| 1 | 1.28 (m) | —CH$_2$ |
| 2 | 2.69 (t) | —O—CH$_2$ |
| 3 | 2.81 (m) | —N—CH$_2$ |
| 4 | 3.30 (t) | Ar—CH$_2$— |
| 5 | 3.34 (t) | N—CH$_2$ |
| 6 | 7.76 (b) | NH$_2$ |
| 7 | 8.47 (s) | Ar—H |

Br-DNI-GABA MS Spectra:

| Molecular formula | exact weight | (m/z)$^+$ |
|---|---|---|
| C12H13BrN4O5 | 372.01 | 373 |

EXAMPLE 15

Neutralisation of Glutamic Acid Formed by the Spontaneous Hydrolysis of DNI-Glu*TFA Using a Composition Containing L-Glutamic Acid Dehydrogenaze and β-Nicotinamide Adenine Dinucleotide Phosphate The composition according to Example 9 was dissolved in 12 ml ACSF solution in an amount which was calculated on the basis of Example 8. The obtained solution can be used directly in one- or two-photon extinction tests.

Two-Photon Irradiation Tests

EXAMPLE 16

The Use of MNI-Glu*TFA and DNI-Glu*TFA in Two-Photon Irradiation Tests on Biological Samples Reference Example Slice Preparation and the Environments of Electrophysiology Tests Acute hippocampus slices were prepared from 16-20 day old Wistar rats using isoflurane anaesthesia followed by swift decapitation. The process was in accordance with the Hungarian Act of Animal Care and Experimentation (1998. XXVIII, section 243). Coronal (300 μm) brain slices were cut with a vibratome and stored at room temperature in artificial cerebrospinal fluid (ACSF). The composition of the ACSF solution is described above.

Hippocampus neurons in CA1 stratum radiatum near the border of the stratum lacunosum-moleculare were visualized using 900 nm infrared oblique illumination. Current-clamp recordings were made at 32° C. (MultiClamp 700B, Digidata 1440; Molecular Devices, Sunnyvale, Calif., USA) with glass electrodes (6-9 MΩ) filled with (in mM): 125 K-gluconate, 20 KCl, 10 HEPES, 10 Di-Tris-salt phosphocreatine, 0.3 Na-GTP, 4 Mg-ATP, 10 NaCl, 0.06 Oregon Green BAPTA-1 (OGB-1) and biocytin. Cells with a resting membrane potential more negative than −50 mV were accepted. The recorded cells were classified as nonpyramidal cells according to their electrophysiological properties.

Two-Photon Imaging

Two-photon imaging started 15-20 minutes after attaining the whole-cell configuration on a two-photon laser-scanning system (Femto2D, Femtonics Ltd., Budapest) using femtosecond lasers (830-850 nm), Mai Tai HP, SpectraPhysics, Mountain View, Calif.). Multiple Line Scanning Method (Femtonics) was used for imaging long dendritic segments. At the end of each experiment, a series of images across the depth of the volume encompassing the imaged neuron was taken Measurement control, real-time data acquisition and analysis were performed with a MATLAB based program (MES, Femtonics Ltd., Budapest) and by a software written by the user.

Two-Photon Uncaging a.) After achieving the whole-cell mode and filling the interneurons with 60 μM OGB-1, the bath solution was exchanged to ACSF containing MNI-Glu-TFA [2.5 mM, Tocris]. Photolysis of MNI-Glu-TFA was performed with 710-830 nm ultrafast, pulsed laser light (Mai Tai HP Deep See, SpectraPhysics, Mountain View, Calif.). The intensity of the uncaging laser beam was controlled with an electro-optical modulator (Model 350-80 LA, Conoptics). Dispersion compensation was set to have maximal response at the depth of uncaging (50-80 μm from surface). The uncaging laser beam was coupled into the imaging optical pathway with a dichroic mirror (custom laser combiner, z750bcm; Chroma Technology Corp, Rockingham, USA). Chromatic aberration was compensated at the focal plane. Radial and axial beam (imaging and photochemical stimulating) alignment errors were held below 100 nm and 300 nm, respectively. Imaging was interleaved with two-photon glutamate uncaging periods, when galvanometers jumped to the maximum 15-25 selected locations (<60 μs jump time) and returned back to the 3D or 2D trajectory thereafter. The position of uncaging sites was finely adjusted according to background images taken. Photolysis of caged glutamate was performed in "clustered" (0.8±0.1 μm distance between inputs) patterns along the dendrite. The single spot uncaging time and laser intensity was set to reproduce uEPSPs and mEPSPs induced by the local application of high osmolar external solution at similar distances from the soma (amplitude of unitary gluEPSP: 0.56±0.09 mV, mEPSPs: 0.58±0.1, uEPSP: 0.55±0.12; exposure time 0.2-0.5 ms/input). Small drifts of the sample (on the order of 0.1-0.2 μm) during the mapping were compensated manually according to regularly taken background images.

b.) After the test the perfusion rate was set to 10 ml/min in order to increase the exchange rate of ACSF containing 2.5 mM DNI-Glu*TFA used in the subsequent test. The test was repeated with the same setting of the equipment on the same dendrite section.

EXAMPLE 17

The change of the spontaneous activity of the cell due to the addition of a caged compound and an enzyme in a voltage-clamp test.

(FIG. 1)

A.) Using the test setup of the two-photon excitation process according to Example 16 spontaneous potential changes of the observed cell was measured.

Figure 1B:
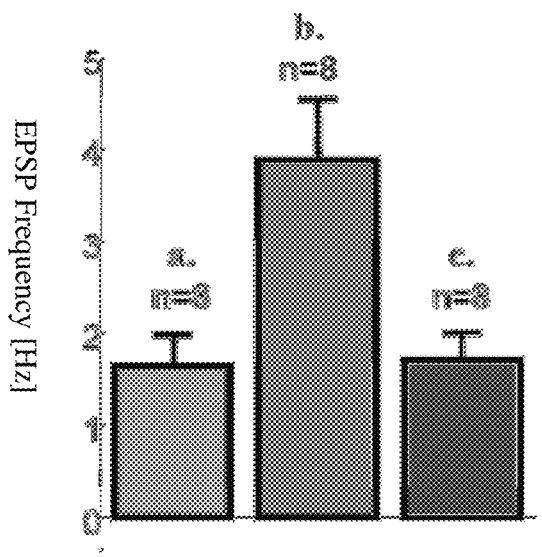
FIG. 1B—Graph showing EPSP Frequency [Hz] according to Example 17.

At the beginning of the experiment the control level of potential changes (EPSP) was measured in the absence of DNI-Glu. The measured fluctuation is shown in FIG. 1/A. Following the test DNI-Glu (2.5 mM) was added to the measuring cell. The measured fluctuation is shown in FIG. 1/B. Then 0.1-0.2 unit/ml L-glutamic acid dehydrogenase enzyme and 200 μM NADP (β-Nicotinamide adenine dinucleotide phosphate) were added. The measured fluctuation is shown in FIG. 1/C. These Figures show that the frequency of spontaneous responses restored to the control level.

B.) The experiment described in point A.) was repeated 8 times using other cells in each case. The column diagram can be seen on the left side. The average of the control level is shown in column a.). The average of the change due to the caged compound is shown in column b.), while the average level after the addition of the enzyme in column c.).

Results of the Tests:

|  | Control, column a.) | DNI-Glu, column b.) | DNI-Glu + enzyme c.) |
| --- | --- | --- | --- |
| MEAN [Hz] | 1.64 | 3.87 | 1.71 |
| SEM | 0.34 | 0.67 | 0.29 |
| STD | 0.95 | 1.9 | 0.81 |

Due to the fact that with the addition of the enzyme the frequency of the potential fluctuation can be reduced to the control level, thus the background noise in the one- or multi-photon, preferably in two-photon experiments reduced, thus the experiments can be carried out with a higher accuracy and reproducibility and the risk of cell death is also reduced.

EXAMPLE 18

Use of MNI-Glu*TFA and DNI-Glu*TFA in Two-Photon Experiments in Biological Samples in the Presence of Agents which Neutralize the Amino Acids Formed by Spontaneous Hydrolysis of Caged Compounds The experiment was carried out according to Example 16 with the difference that to the ACSF solution containing 2.5 mM MNI-Glu*TFA in the first measurement and to the ACSF solution containing 2.5 mM DNI-Glu*TFA in the second measurement 0.1-0.2 units/ml of L-glutamic acid and 200 μM β-Nicotinamide adenine dinucleotide phosphate were added in the sample chamber.

Figure 2A:
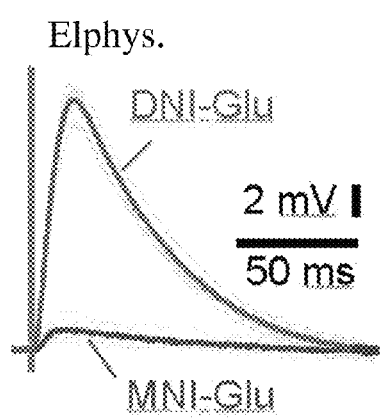
FIG. 2A—Shows Elphys comparison of biological effects of DNI and MNI type compounds according to Example 18.
Figure 2B:
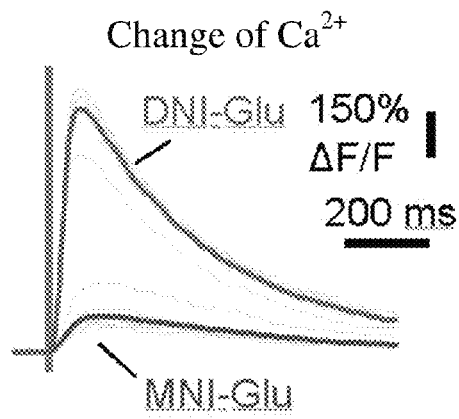
FIG. 2B—Shows Change of $Ca^{2+}$ comparison of biological effects of DNI and MNI type compounds according to Example 18.
Figure 3A:
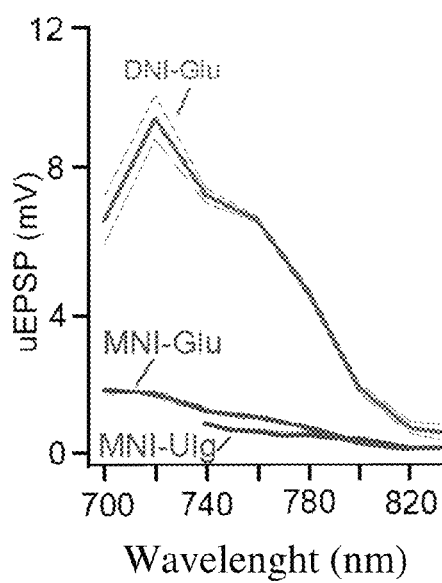
FIG. 3A—Shows uEPSP (mV) comparison of biological effects of DNI and MNI type compounds depending on the wavelength of the used light.
Figure 3B:
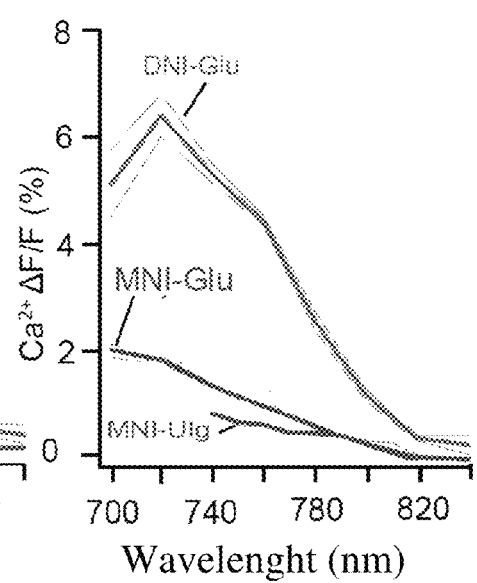
FIG. 3B—Shows $Ca^{2+}\Delta F/F$ (%) comparison of biological effects of DNI and MNI type compounds depending on the wavelength of the used light.

The experiments were repeated several times. The results are shown in FIG. 2. According to the experiments the excitation postsynaptic potential (EPSP) is significantly higher using DNI-Glu than in case of using MNI-Glu. These results are shown in FIG. 2/A, in which the horizontal scale bar means 50 ms of time unit, and the vertical scale bar means 2 mV of voltage. FIG. 2/B shows that the $Ca^{2+}$ transient signal is also significantly higher in case of using DNI-Glu than MNI-Glu as a response of the irradiation.

EXAMPLE 19

Use of MNI-Glu*TFA and DNI-Glu*TFA in Two-Photon Experiments on Biological Samples in the Presence of Agents which Neutralize the Amino Acids Formed by Spontaneous Hydrolysis of Caged Compounds The experiments were carried out in accordance of the Example 16 with the following differences: after patch clamp the perfusion solution exchange to ACSF containing 2.5 mM MNI-Glu TFA and, or ACSF containing 2.5 mM DNI-Glu TFA, 0.1-0.2 units/ml of L-glutamic acid dehydrogenase and β-Nicotinamide adenine dinucleotide phosphate for the second measurement. The β-Nicotinamide adenine dinucleotide phosphate was kept in a concentration of 50-100 μM during the experiments. All chemical agents (cage compound, dehidrogenase, NADP apply into the bath).

EXAMPLE 20

Examination of the Effects of iDMPO-DNI-Glutamic Acid and iDMBO-DNI-Glutamic Acid in the Presence of Agents which Neutralize the Amino Acids Formed by Spontaneous Hydrolysis of Caged Compounds The experiment was carried out according to Example 16 with the difference that the cell was filled with calcium sensitive dye (Fluo4) and anatomical dye (ALEXA 594). The experiments were carried out in accordance of the Example 16 with the following differences: after patch clamp the perfusion solution exchange to ACSF containing 2.5 mM iDMPO-DNI-Glutamic acid*2TFA and, or ACSF containing 2.5 mM iDMBO-DNI-Glutamic acid*2TFA, 0.1-0.2 units/ml of L-glutamic acid dehydrogenase and β-Nicotinamide adenine dinucleotide phosphate for the second measurement. The β-Nicotinamide adenine dinucleotide phosphate was kept in a concentration of 50-100 μM during the experiments. All chemical agents (cage compound, dehidrogenase, NADP apply into the bath). During the experiments the evaporation loss of $dH_2O$ was continuously refilled.

Figures 4A, 4B, 4C, 4D, 4E:
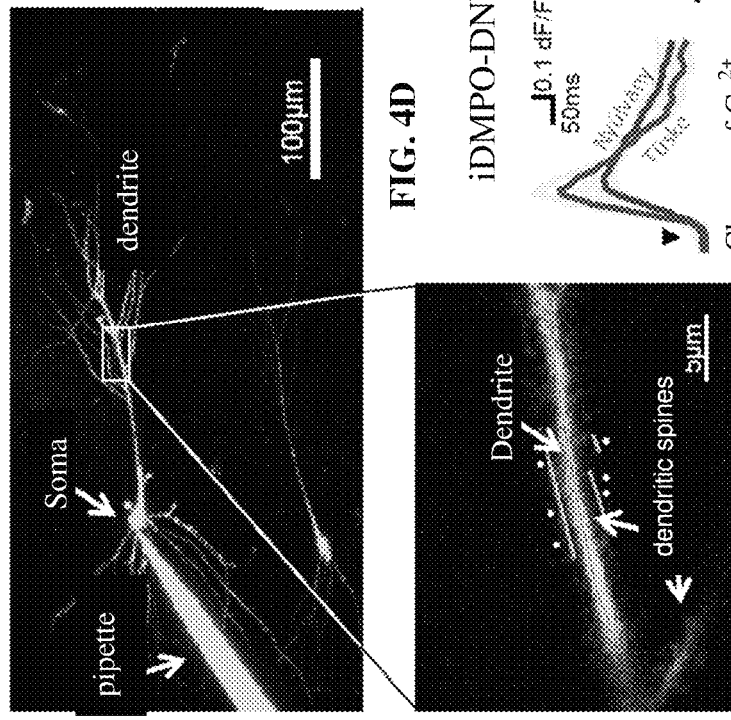
FIG. 4A—Shows the comparison of biological effects of iDMPO-DNI-Glutamate and iDMPO-DNI-Glutamate compounds on a neuron according to Example 20.
FIG. 4B—Shows an alternative comparison of biological effects of iDMPO-DNI-Glutamate and iDMPO-DNI-Glutamate compounds on a neuron according to Example 20.
FIG. 4C—Shows an alternative comparison of biological effects of iDMPO-DNI-Glutamate and iDMPO-DNI-Glutamate compounds on a neuron according to Example 20.
FIG. 4D—Shows an alternative comparison of biological effects of iDMPO-DNI-Glutamate and iDMPO-DNI-Glutamate compounds on a neuron according to Example 20.
FIG. 4E—Shows an alternative comparison of biological effects of iDMPO-DNI-Glutamate and iDMPO-DNI-Glutamate compounds on a neuron according to Example 20.
Figure 5C:
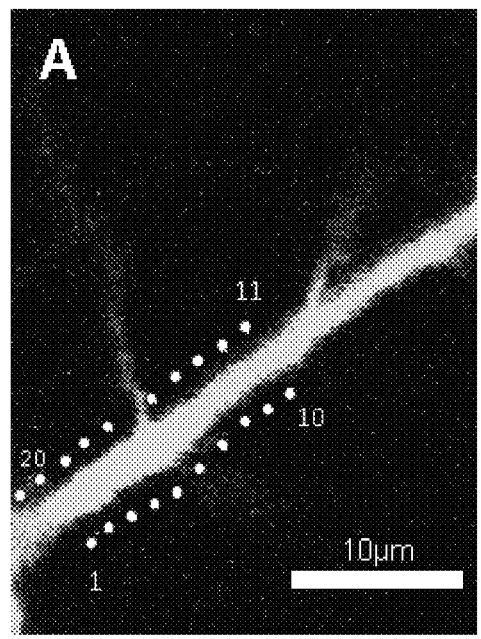
FIG. 5C—Shows the receptor density on each section based on the responses to stimulation of the neurobiological examination of a neuron with a two-photon irradiation method using iDMPO-DNI-GABA*2 TFA as caged compound.
Figure 5C:
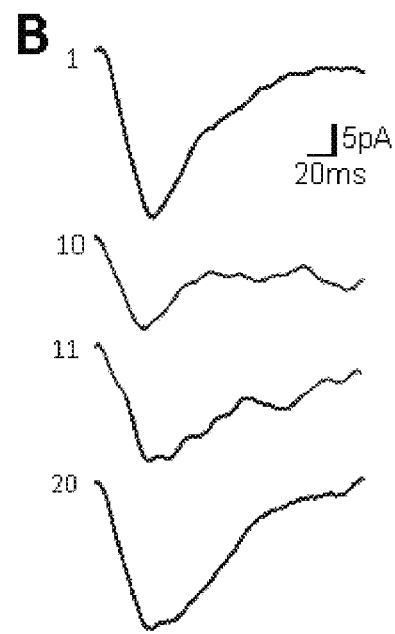
Figure 5C:
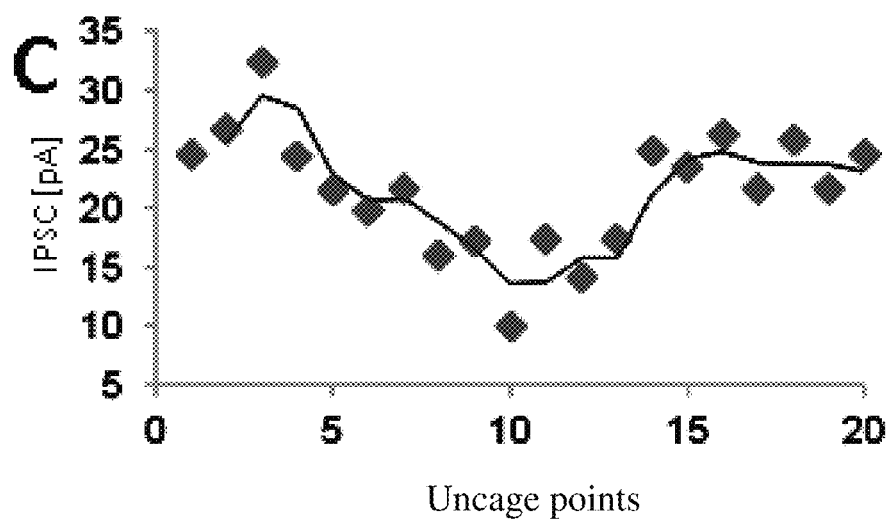

The results of the experiments are shown in FIG. 4 as follows:

(A) Two-photon maximum intensity stack projection microscopic image of a hippocampal pyramide cell. The cell was filled with calcium sensitive dye (Fluo4) and anatomical dye (ALEXA 594). The white frame shows the measuring area, which is enlarged on panel (C). B shows the typical cell response of a pyramid cell for a somatically induced and led 500 ms long −100, 0 and 125 pA current injection. The waveform did not change significantly due to the stimulation, toxicity was not detected. The (C) panel is the two-photon microscopic image of the dendrite of the pyramid cell. White points indicate the localization of the photochemical stimulations (740 nm wavelength). Red line indicate the area of the calcium imaging where the calcium concentrations were measured (D) Calcium tranziens (left) and somatically recorded EPSP (right) could evoke by two-photon stimulation with a presence of iDMPO-DNI-Glu TFA (2.5 mM). Panel (E) the same as Panel (D) on the presence of the iDMBO-DNI-Glu TFA (2.5 mM). Black arrowheads indicate the moment of the stimulation. The results were detected not only in the dendrite (flatter curves) but in the spine (sharper curve) as well, which show the stimulation precision. The calcium signal appear in the spine (where the glutamate receptors are localized mainly) first and than it spread into the dendrite with smaller amplitude which shows the localisation and sensitivity of the stimulation.

The invention claimed is:

1. A method for the neutralisation of a biologically active compound formed by spontaneous degradation of a photocleavable compound, comprising mono- or multi-photon irradiating a composition comprising said photocleavable compound and a reagent, which reagent is capable of neutralizing a biologically active compound formed by the spontaneous degradation of the photocleavable compound, wherein the photocleavable compound is the trifluoroacetic acid salt of a compound of the formula (I)

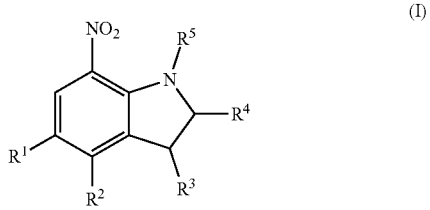

R$^1$ stands for hydrogen atom, or cyano, nitro, carboxyl or formyl group or a halogen atom;
R$^2$ stands for a hydrogen or bromo atom or a hydroxyl group, or
straight or branched alkoxy, or cycloalkoxy, substituted with an unsubstituted amino group, or an amino group substituted with a C$_1$-C$_6$ alkyl group or cycloalkyl group, or two identical or different C$_1$-C$_6$ alkyl groups, aryl group, heteroaryl group or cycloalkyl group; or aryl group;
R$^3$ and R$^4$ stand for hydrogen atoms;
R$^5$ is an acid residue of an amino acid, or
R$^5$ stands for a group of formula (II)

in which the nitrogen atom and the attached R$^6$ and R$^7$ substituents together stand for an amine residue of a neurotransmitter and in which X stands for an oxygen or sulphur atom.

2. The method according to claim 1, wherein R$^5$ in the compound of formula (I) is an acid residue.

3. The method according to claim 1, wherein the biologically active reagent formed by the spontaneous degradation of the photocleavable compound is neutralized by an enzyme, a tissue containing living cells or a cell culture.

4. The method according to claim 1, wherein the reagent which neutralizes the biologically active compound formed by the spontaneous degradation of the photochemically active compound is a solid adsorbent.

5. The method according to claim 1, wherein
R$^1$ stands for a nitro group and
R$^2$ stands for a hydrogen or bromo atom, or
straight or branched alkoxy, or cycloalkoxy, substituted with an unsubstituted amino group, or an amino group substituted with a C$_1$-C$_6$ alkyl group or cycloalkyl group, or two identical or different C$_1$-C$_6$ alkyl groups, aryl group, heteroaryl group or cycloalkyl group.

6. A process for performing a one- or a multi-photon irradiation process, comprising adding a photochemically cleavable compound and a reagent which neutralizes the biologically a compounds formed by spontaneous degradation of the photocleavable compound to a fluid medium containing cells, then mono- or multi-photon irradiating the resultant sample, wherein the photocleavable compound is the trifluoroacetic acid salt of a compound of the formula (I)

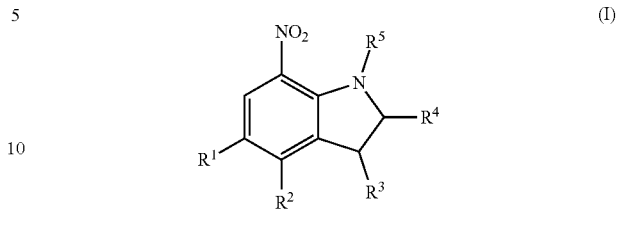

R$^1$ stands for hydrogen atom, or cyano, nitro, carboxyl or formyl group or a halogen atom;
R$^2$ stands for a hydrogen or bromo atom or a hydroxyl group, or
straight or branched alkoxy, or cycloalkoxy, substituted with an unsubstituted amino group, or an amino group substituted with a C$_1$-C$_6$ alkyl group or cycloalkyl group, or two identical or different C$_1$-C$_6$ alkyl groups, aryl group, heteroaryl group or cycloalkyl group; or aryl group;
R$^3$ and R$^4$ stand for hydrogen atoms;
R$^5$ is an acid residue of an amino acid, or
R$^5$ stands for a group of formula (II)

in which the nitrogen atom and the attached R$^6$ and R$^7$ substituents together stand for an amine residue of a neurotransmitter and in which X stands for an oxygen or sulphur atom.

7. The process according to claim 6, wherein the cells are neurons and the reagent which neutralize the biologically active compounds are enzymes.

8. The process according to claim 7, wherein the biologically active compounds formed by the spontaneous degradation of photochemically cleavable compounds are absorbed with a solid ion exchange resin.

9. A trifluoro acetic acid salt of a compound of formula (I)

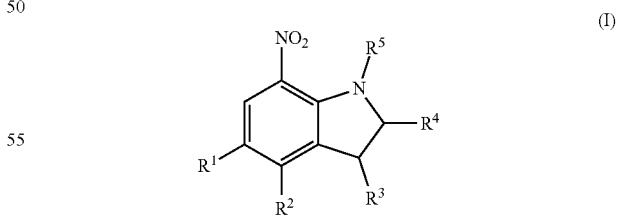

wherein
R$^1$ stands for hydrogen atom, or cyano, nitro, carboxyl or formyl group or a halogen atom;
R$^2$ stands for a hydrogen or bromo atom a hydroxyl group, or
straight or branched alkoxy, or cycloalkoxy, substituted with an unsubstituted amino group, or an amino group substituted with a C$_1$-C$_6$ alkyl group or cycloalkyl group, or two identical or different $C_1$-$C_6$ alkyl groups, aryl group, heteroaryl group or cycloalkyl group;

$R^3$ and $R^4$ stand for hydrogen atoms;

$R^5$ is an acid residue of an amino acid, or $R^5$ stands for a group of the general formula (II)

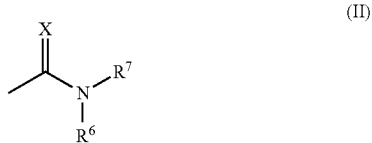

(II)

in which the nitrogen atom and the attached $R^6$ and $R^7$ substituents together stand for an amine residue of a neurotransmitter and in which X stands for an oxygen or sulphur atom.

10. A compound according to claim 9 wherein $R^1$ stands for a nitro group;

$R^2$ stands for a hydrogen or bromo atom, or dimethylamino-ethoxy group, dimethylamino-propoxy, isomers of dimethylamino-isopropoxy group (—O—CH(CH$_3$)CH$_2$—N(CH$_3$)$_2$ and O—CH$_2$—CH(CH$_3$)—CH$_3$)$_2$ groups), dimethylamino-isobutoxy group (O—CH$_2$—CH(CH$_3$)—CH$_2$—N (CH$_3$)$_2$; or aryl group;

$R^3$ and $R^4$ stand for hydrogen atoms;

$R^5$ stands for an acid residue of L-Glutamic acid, GABA or Glycin, or a group of the general formula (II) in which the nitrogen atom and the attached $R^6$ and $R^7$ substituents together stand for an amine residue of L-Glutamic acid, GABA or Glycin and X stands for an oxygen or sulphur atom.

11. A compound according to claim 9, wherein $R^1$ stands for a nitro group and $R^2$ stands for a hydrogen or bromo atom, or straight or branched alkoxy, or cycloalkoxy, substituted with an unsubstituted amino group, or an amino group substituted with a $C_1$-$C_6$ alkyl group or cycloalkyl group, or two identical or different $C_1$-$C_6$ alkyl groups, aryl group, heteroaryl group or cycloalkyl group; or aryl group.

12. A composition comprising photochemically cleavable compounds of the trifluoroacetic acid salt of the compound of the formula (I) according to claim 9 and a reagent which neutralizes the biologically active compounds formed by the degradation of photochemically cleavable compounds and optionally further accessory agents.

13. The composition according to claim 12, wherein the photochemically cleavable compound and the reagent which neutralizes the biologically active compounds of the degradation of the photochemically cleavable compound have been formulated separately.

* * * * *